(12) United States Patent
Balloch et al.

(10) Patent No.: US 12,222,334 B2
(45) Date of Patent: Feb. 11, 2025

(54) USE OF LOW-BIND SURFACE COATINGS FOR ANALYSIS OF TYROSINE KINASE INHIBITORS

(71) Applicant: Micromass UK Limited, Wilmslow (GB)

(72) Inventors: Stephen Balloch, Stockport (GB); Lisa Jane Calton, Stockport (GB); Gareth Hammond, Stockport (GB)

(73) Assignee: Micromass UK Limited, Wilmslow (GB)

( * ) Notice: Subject to any disclaimer, the term of this patent is extended or adjusted under 35 U.S.C. 154(b) by 303 days.

(21) Appl. No.: 17/730,271

(22) Filed: Apr. 27, 2022

(65) Prior Publication Data

US 2022/0341896 A1    Oct. 27, 2022

Related U.S. Application Data

(60) Provisional application No. 63/180,364, filed on Apr. 27, 2021.

(51) Int. Cl.
| | | |
|---|---|---|
| *G01N 30/16* | (2006.01) | |
| *G01N 30/72* | (2006.01) | |
| *G01N 33/94* | (2006.01) | |
| *G01N 30/02* | (2006.01) | |

(52) U.S. Cl.
CPC ......... *G01N 30/16* (2013.01); *G01N 30/7233* (2013.01); *G01N 33/94* (2013.01); *G01N 2030/027* (2013.01)

(58) Field of Classification Search
CPC .... G01N 30/16; G01N 30/7233; G01N 33/94; G01N 2030/027; G01N 30/72; G01N 2030/524; G01N 30/88; G01N 2030/8831; G01N 33/50
USPC ....... 73/61.52, 61.53, 61.55, 64.21; 210/656, 210/657, 198.2; 422/70; 435/3, 803, 108
See application file for complete search history.

(56) References Cited

U.S. PATENT DOCUMENTS

2009/0071834 A1    3/2009    Hafeman et al.

FOREIGN PATENT DOCUMENTS

WO        2007126913 A1    11/2007

OTHER PUBLICATIONS

International Search Report and Written Opinion issued in International Application No. PCT/GB2022/051065 dated Aug. 5, 2022.

*Primary Examiner* — Robert R Raevis
(74) *Attorney, Agent, or Firm* — WOMBLE BOND DICKINSON (US) LLP; Deborah M. Vernon; Mark R. DeLuca

(57) ABSTRACT

The present disclosure discusses a method of separating a sample of tyrosine kinase inhibitors or metabolites of tyrosine kinase inhibitors which includes injecting the sample into the chromatographic system having one or more low-bind coated surfaces along the flow path; flowing the sample through the chromatographic system; separating the sample; and analyzing the separated sample. Consequently, the sample does not bind to the low-binding surface coatings (e.g., alkylsilyl coatings) of the flow path. The applied coating can reduce peak tailing and decrease carryover for tyrosine kinase inhibitor samples during chromatographic analysis.

14 Claims, 17 Drawing Sheets

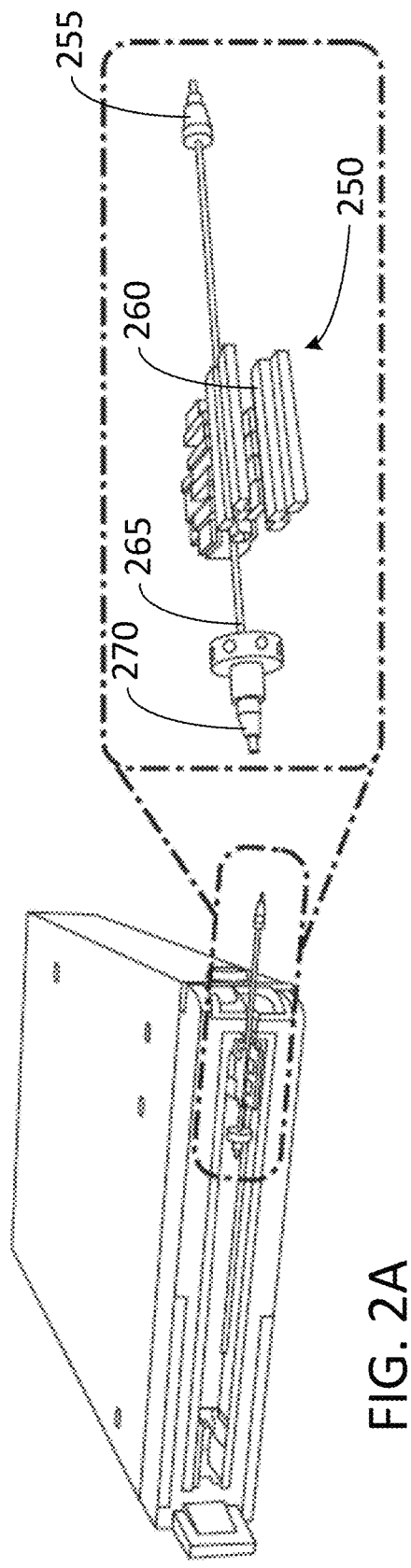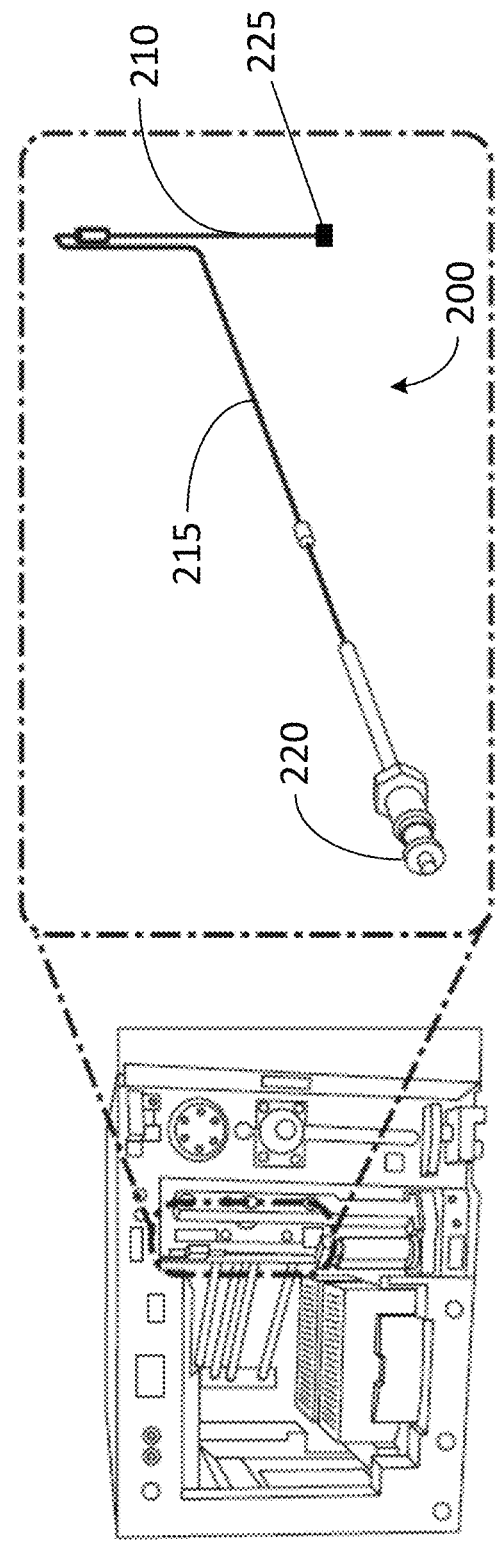
FIG. 2A
FIG. 2B
FIG. 2C
FIG. 2D

Norimatinib

Nilotinib

Imatinib

Dasatinib

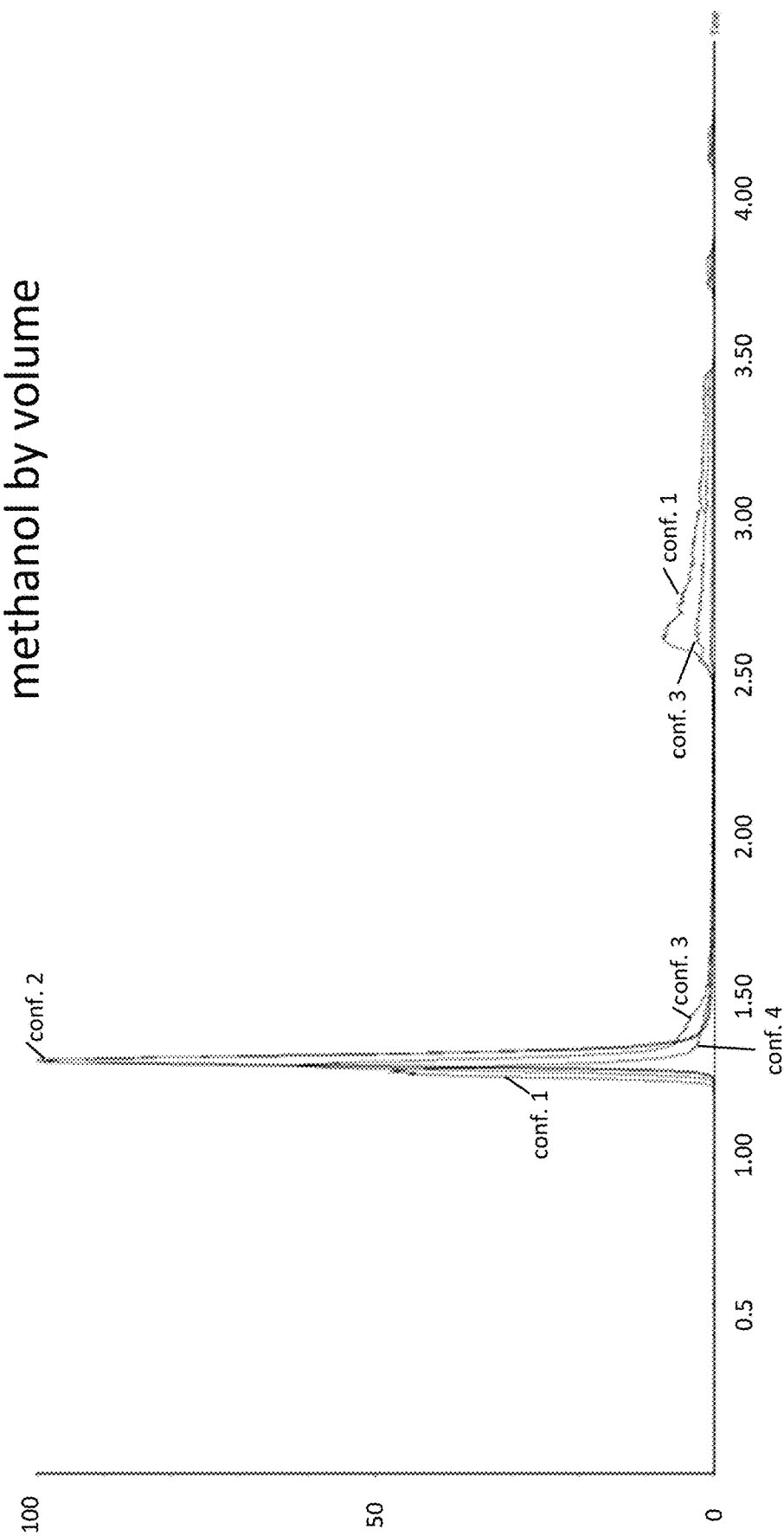

USE OF LOW-BIND SURFACE COATINGS FOR ANALYSIS OF TYROSINE KINASE INHIBITORS

CROSS-REFERENCE TO RELATED APPLICATIONS

This application claims priority to and the benefit of U.S. Provisional Application No. 63/180,364, filed Apr. 27, 2021, and entitled "Use of Low-Bind Surface Coatings for Analysis of Tyrosine Kinase Inhibitors." The foregoing application is incorporated herein by reference in its entirety.

FIELD OF THE TECHNOLOGY

The present disclosure relates to the use of coated flow paths for improved chromatography and sample analysis of tyrosine kinase inhibitors. More specifically, this technology relates to separating analytes in a sample using chromatographic devices having coated flow paths, methods of separating analytes in a sample (for example, tyrosine kinase inhibitors in a plasma or serum sample) using a fluidic system that includes coated flow paths, and methods of tailoring a fluidic flow path for separation and analysis of tyrosine kinase inhibitors.

BACKGROUND

Analytes that interact with metal have often proven to be very challenging to separate. The desire to have high pressure capable chromatographic systems with minimal dispersion has required that flow paths decrease in diameter and be able to withstand increasingly high pressures at increasingly fast flow rates. As a result, the material of choice for chromatographic flow paths is often metallic in nature. This is despite the fact that characteristics of certain analytes, for example, small molecule pharmaceutical agents, proteins, glycans, peptides, oligonucleotides, pesticides, bisphosphonic acids, anionic metabolites, and zwitterions like amino acids and neurotransmitters, are known to have unfavorable interactions, so called chromatographic secondary interactions, with metallic surfaces.

The proposed mechanism for metal specific binding interactions requires an understanding of the Lewis theory of acid-base chemistry. Pure metals and metal alloys (along with their corresponding oxide layers) have terminal metal atoms that have characteristics of a Lewis acid. More simply, these metal atoms show a propensity to accept donor electrons. This propensity is even more pronounced with any surface metal ions bearing a positive charge. Analytes with sufficient Lewis base characteristics (any substance that can donate non-bonding electrons) can potentially adsorb to these sites and thus form problematic non-covalent complexes. It is these substances that are defined as metal-interacting analytes.

Many small molecule pharmaceutically active agents intrinsically contain oxygen-containing and nitrogen-containing residues that act as Lewis bases. These groups have the ability to interact with metals in the flow path through non-bonding electron interactions. This curtails the overall effective separation of biomolecules such as peptides. Most, if not all, tyrosine kinase inhibitors are composed of a one or more aromatic and/or aliphatic heterocycle rings that include such oxygen, nitrogen or sulfur atoms.

An alternative to using metal flow paths is to use flow paths constructed from polymeric materials, such as polyether ether ketone (PEEK). PEEK tubing, like most polymeric materials, is formed by means of an extrusion process. With polymeric resin, this manufacturing process can lead to highly variable internal diameters. Accordingly, PEEK column hardware yields unfavorable differences in the retention times as can be observed from switching between one column and the next. Often, this variation can be a factor of three higher than a metal constructed column.

Ongoing efforts to reduce chelation and secondary chromatographic interactions of analytes with metal chromatographic surfaces in an effort to facilitate chromatographic separation having higher resolutions are therefore needed. In addition, variability in the separation and detection of compounds can be caused by many factors. One such factor is analyte/surface interactions of compounds with the analytical column. Such interactions can be problematic, especially at very low concentrations of analytes. This has been found to be especially true for tyrosine kinase inhibitors.

SUMMARY

Secondary interaction or adsorption of metal sensitive analytes to active sites dispersed throughout the metallic surface in liquid chromatography based separations have often been challenging to separate. To address problems experienced in separations in metallic fluidic systems, column hardware using a coating has been developed to define a low-bind surface coating. Column hardware with low-bind surface coatings can positively impact chromatographic performance in terms of band broadening, peak tailing, and/or recovery which in turn can increase resolution, peak capacity, and/or quantitative accuracy of liquid chromatography-based assays, and in particular liquid chromatography-based peptide mapping assays.

The therapeutic activity of TKIs can be optimized by establishing an individualized dosage regime. The optimal dosage regime can be determined by measurement of the drug concentration, or metabolites produced after administration of the drug, in the blood of subjects receiving TKIs as part of their cancer chemotherapy. High Pressure Liquid Chromatography (HPLC) has been found to be an effective technique for monitoring blood concentrations of TKIs and TKI metabolites. It has been found, however, that many TKIs and TKI metabolites can interact with stainless steel flow path tubing to create poor peak intensity, strong tailing and a large amount of carryover. This is of concern in industry where routine assays are expected to perform with consistent and accurate results. Recent observations have shown that column and LC hardware should also be given serious consideration to improve assay reproducibility and sensitivity. Specifically, metal-ion mediated adsorption in liquid chromatography (LC) has been observed as a contributing factor to poor peak shape, tailing, and diminished recovery of sensitive analytes. By utilizing chromatography system components having a low-bind surface coating along at least some portions of the fluidic pathway, improvements can be achieved in assay sensitivity, recovery, and reproducibility.

In addition, for tyrosine kinase inhibitor analysis sample throughput can be increased by using the technology of the present disclosure. Sample throughput can be increased by reduced peak tailing and increased resolution. For example, if impurities are closely eluting with the native peak and the native peak was exhibiting a degree of tailing, a user (e.g., an analyst) may try to extend the gradient or run-time to resolve impurities to an acceptable resolution between peaks that facilitated accurate quantitation. In the absence of tailing, a user could shorten the run time by using a steeper slope in the gradient. This could effectively elute everything faster and closer together. But the resolution between peaks, while decreasing, may still be sufficient for the assay since tailing is not present to interfere with integration or cause a co-elution. With reduced peak tailing, new trace species can be detected by being able to see peaks that were formerly covered by peak tailing.

Additionally, increased resolution or more time between peaks can allow a user to run faster methods with increased throughput. If resolution has increased, then peak capacity increases meaning more peaks can fit in the same chromatogram or a faster separation could be run at the cost of resolution and peak capacity if the critical pair of interest were resolved sufficiently to start with.

The present technology includes a coating, such as an alkylsilyl coating, that can provide a low-bind surface coating to reduce peak tailing and increase stability of the tailing factor from initial injection of a sample onward, increase analyte recovery, increase sensitivity, as well as reproducibility by minimizing the analyte/surface interactions that can lead to sample losses. Additionally, low-bind surface coated hardware does not appear to adversely affect chromatographic performance or recovery of tyrosine kinase inhibitors. For example, similar retention times were observed for LBS coated and non-coated surfaces.

An alkylsilyl coating on the surface area defining the flow path of a chromatographic system (e.g., a fluid-contacting coating covering metallic surfaces) can minimize the interactions between tyrosine kinase inhibitors and the metallic surfaces of chromatographic flow paths. Consequently, the coated metallic surfaces improve liquid chromatography separations for tyrosine kinase inhibitors. The use of alkylsilyl coatings on metal flow paths allows the use of metal chromatographic flow paths, which are able to withstand high pressures at fast flow rates, high pressure generated using stationary phases with small particles (which can be slow flow as well), and high pressure generated from longer column beds, while minimizing the secondary chromatographic interactions between the analytes and the metal. These components made of high-pressure material and modified with a coating can be tailored so that the internal flow paths reduce secondary chromatographic interactions. The coating covers the metallic surfaces that are exposed to the fluidic path (i.e., a fluid-contacting coating).

In one aspect, the present technology is directed to a method of separating and analyzing tyrosine kinase inhibitors in a sample. The method includes injecting a sample including one or more tyrosine kinase inhibitors into a chromatographic system. The sample can be prepared from plasma or serum obtained from a subject. The subject may be undergoing chemotherapy by administration of one or more tyrosine kinase inhibitors. The chromatographic system includes a metallic flow path. At least a portion of the metallic flow path is coated with a low-bind surface coating. The sample is flowed through the chromatographic system, separating the one or more tyrosine kinase inhibitors form other components in the plasma or serum. The separated tyrosine kinase inhibitors are passed to a detector.

In an embodiment, the method further comprises analyzing the separated tyrosine kinase inhibitors to determine an identity and/or amount of tyrosine kinase inhibitors present in the plasma or serum. Analysis of plasma or serum may include injection of a sample including two or more tyrosine kinase inhibitors. The method may include separating the two or more tyrosine kinase inhibitors from each other and determining an identity and/or amount of each separated tyrosine kinase inhibitor. In some embodiments, the tyrosine kinase inhibitors include at least one of imatinib, norimatinib (N-desmethyl imatinib), dasatinib, and nilotinib.

In an embodiment, the chromatographic system comprises a sample injector comprising a sample needle and a needle port, a pre-column heater coupled to the sample injector and a chromatography column coupled to the pre-column heater, wherein injecting the sample comprises drawing the sample into the chromatographic system through the sample injector and passing the sample through the pre-column heater before the sample enters the chromatography column. The metal tubing portions of the sample needle can be coated with the low-bind surface coating. The needle port can be coated with the low-bind surface coating. The metal portions of the pre-column heater may be coated with the low-bind surface coating. In an embodiment, any combination of the needle port, the metal tubing portions of the sample needle, and the metal tubing portions of the pre-column heater is coated with a low-bind surface coating.

In an embodiment, the low-bind surface coating is an alkylsilyl coating. The alkylsilyl coating can be bis(trimethoxysilyl)ethane or bis(tirchlorosilyl)ethane. The alkysilyl coating can be a first alkylsilyl coating layer in contact with the portion of the metallic flow path and a second alkylsilyl coating layer formed on the first alkylsilyl coating layer. The first coating layer can be bis(trimethoxysilyl)ethane or bis(tirchlorosilyl)ethane and the second coating layer can be n-dec yltrichloro silane.

In an embodiment, the detector is a mass spectrometer.

BRIEF DESCRIPTION OF THE DRAWINGS

The technology will be more fully understood from the following detailed description taken in conjunction with the accompanying drawings, in which:

FIG. 2A is a schematic diagram of a pre-column heater.

FIG. 2B is an exploded view of the pre-column heater of FIG. 2A.

FIG. 2C is a schematic diagram of a sample injector having a sample needle and a needle port.

FIG. 2D is an exploded view of the sample injector of FIG. 2C.

FIG. 6A shows an overlay of chromatograms obtained from HPLC analysis of a sample of imatinib in methanol (25% by volume) using four different chromatography system configurations having different combinations of original (uncoated) and coated components (sample needle and/or pre-column heater).

DETAILED DESCRIPTION

Figure 1:
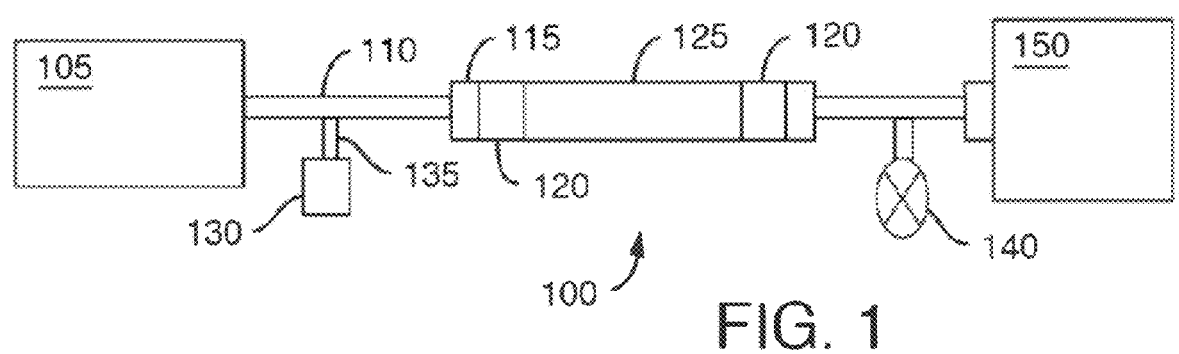
FIG. 1 is a schematic of a chromatographic flow system including a chromatography column and various other components, in accordance with an illustrative embodiment of the technology. A fluid is carried through the chromatographic flow system with a fluidic flow path extending from a fluid manager to a detector, such as a MS detector.

In general, the present disclosure is related to coating flow path components to have low-binding surface coatings to increase analyte recovery, reproducibility and sensitivity by minimizing negative analyte/surface interactions that can lead to sample losses. The present disclosure specifically addresses this problem in the context of analyzing the blood plasma or serum concentrations of tyrosine kinase inhibitors in subjects.

Tyrosine kinase inhibitors (TKIs) are small molecule pharmacological agents that inhibit tyrosine kinases. Tyrosine kinases are enzymes that are part of many cell functions including cell signaling, cell growth and cell division. If these enzymes are too active, or found at high concentrations, cells growth may be abnormally effected, leading to cancer. Inhibition of tyrosine kinases (e.g., by administering TKIs) can restore normal cell growth by inhibiting the rapid growth of cancer cells. Examples of TKIs include, but are not limited to: axitinib (INLYTA); dasatinib (SPRYCEL); erlotinib (TARCEVA); imatinib (GLEEVEC); nilotinib (TASIGNA); pazopanib (VOTRIENT); sunitinib (SUTENT); bosutinib (BOSULIF); ponatinib (ICULUSIG); gefitinib (IRES SA); sorafenib (NEXAVAR); lapatinib (TYVERB); crizotinib (XALKORI); vandetanib (CAPRELSA); cabozantinib (COMETRIQ); regorafenib (STIVARGA); trametinib; afatinib (GILOTRIF); vemurafenib (ZELBORAF); ruxolitinib (JAKAVI); apatinib; alectinib; ceritinib; cobimetinib; lenvatinib; osimertinib; neratinib; brigatinib; icotinib; pyrotinib; binimetinib; anlotinib; fruquintinib; lorlatinib; larotrectinib; dacomitinib; erdafitinib; entrectinib; tepotinib; capmatinib; pemigatinib; ripretinib; avapritinib; tucatinib; selumetinib; pralsetinib; selpercatinib; and almonertinib. The method may also work on metabolites of any of these active agents. For example, as shown herein, norimatinib is the N-desmethyl metabolite of imatinib and can be analyzed using the same method.

The therapeutic activity of TKIs can be optimized by establishing an individualized dosage regime. The optimal dosage regime can be determined by measurement of the drug concentration, or metabolites produced after administration of the drug, in the blood of subjects receiving TKIs as part of their cancer chemotherapy. This is particularly important for TKIs, which exhibit high inter-individual variability for therapeutic and toxic effects.

High Pressure Liquid Chromatography (HPLC) has been found to be an effective technique for monitoring blood concentrations of TKIs and TKI metabolites. It has been found, however, that many TKIs and TKI metabolites can interact with stainless steel flow path tubing to create poor peak intensity, strong tailing, and a large amount of carry-over. These side effects of the interaction of TKIs and TKI metabolites with the metal housing can lead to inaccurate analysis of the levels of TKIs in the subject. It has been found that the use of low-bind surface coatings in the flow path of the chromatography system will lead to improvement in peak height, improvement in peak shape and reduced post elution signal (reduced carryover) for TKIs and TKI metabolites.

In addition to improvements for the analysis of TKIs and TKI metabolites, coating the metal flow path components to have low-bind surface coatings minimizes uncertainty of the chromatographic system performance. Permanent passivation (or at least semi-permanent passivation, i.e., useable lifetime of a consumable) can be provided by the coating. For example, the system does not need to be passivated after each wash, and passivation does not effectively diminish after each wash or flowing. Consequently, the analyte detected using LC and a detector (e.g., MS, UV (for abundant species), etc.) can be depended upon as an accurate assessment of the analyte present.

One method of coating metal flow path components with a low-bind surface coating is the use of alkylsilyl coatings. In some aspects, the alkylsilyl coating acts a bioinert, low-bind surface coating to modify a flow path to address flow path interactions with an analyte, such as a metal-sensitive analyte. That is, the bioinert, low-bind surface coating minimizes surface reactions with the metal interacting compounds and allows the sample to pass along a flow path without clogging, attaching to surfaces, or change in analyte properties. The reduction/elimination of these interactions is advantageous because it allows for accurate quantification and analysis of a sample containing metal-sensitive compounds, such as a sample containing low-bind surface coatings. The coating which creates the low-binding surface coating along the flow path prevents/significantly minimizes analyte loss to the metallic surface walls, thereby reducing secondary chromatographic interactions.

FIG. 1 is a representative schematic of a chromatography system 100 that can be used to separate analytes, such as TKIs or TKI metabolites, in a sample. Chromatographic flow system 100 includes several components including a fluid manager system 105 (e.g., controls mobile phase flow through the system), tubing 110 (which could also be replaced or used together with micro fabricated fluid conduits), fluid connectors 115 (e.g., fluidic caps), frits 120, a chromatography column 125, a sample injector 135 including a needle (not shown) to insert or inject the sample into the mobile phase, a vial, sinker, or sample reservoir 130 for holding the sample prior to injection, and a detector 150, such as a mass spectrometer. Interior surfaces of the components of the chromatographic system/device form a fluidic flow path that has wetted surfaces. The fluidic flow path can have a length to diameter ratio of at least 20, at least 25, at least 30, at least 35 or at least 40.

At least a portion of the wetted surfaces can be converted to low-bind surface coating by coating with an alkylsilyl coating to reduce secondary interactions and tailor hydrophobicity of the surfaces. The coating can be applied by vapor deposition. As such, methods and devices of the present technology provide the advantage of being able to use high pressure resistant materials (e.g., stainless steel) for the creation of the flow system, but also being able to tailor the wetted surfaces of the fluidic flow path to provide the appropriate hydrophobicity so deleterious interactions or undesirable chemical effects on the sample can be minimized. In some examples, the coating of the flow path is non-binding with respect to the analyte, such as a metal-sensitive compound (e.g., a TKI). Consequently, the analyte does not bind to the coating of the flow path.

The alkylsilyl coating can be provided throughout the system from the tubing or fluid conduits 110 extending from the fluid manager system 105 all the way through to the detector 150. The coatings can also be applied to portions of the fluidic fluid path (e.g., at least a portion of the fluidic path). That is, one may choose to coat one or more components or portions of a component and not the entire fluidic path. For example, the internal portions of the sample injector 135 and the tubing 110 can be coated whereas the remainder of the flow path can be left unmodified. Further, removable/replaceable components can be coated. For example, the vial or sinker 130 containing the sample reservoir can be coated as well as frits 120.

In one aspect, the flow path of the fluidic systems described herein is defined at least in part by an interior surface of tubing. In another aspect, the flow path of the fluidic systems described herein is defined at least in part by an interior surface of microfabricated fluid conduits. In another aspect, the flow path of the fluidic systems described herein is defined at least in part by an interior surface of a column. In another aspect, the flow path of the fluidic systems described herein is defined at least in part by passageways through a frit. In another aspect, the flow path of the fluidic systems described herein is defined at least in part by an interior surface of a sample injection needle. In another aspect, the flow path of the fluidic systems described herein extends from the interior surface of a sample injection needle throughout the interior surface of a column. In another aspect, the flow path extends from a sample reservoir container (e.g., sinker) disposed upstream of and in fluidic communication with the interior surface of a sample injection needle throughout the fluidic system to a connector/port to a detector. That is, all tubing, connectors, frits, membranes, sample reservoirs, and fluidic passageways along this fluidic path (wetted surfaces) are coated.

In one embodiment, the chromatographic system may include a pre-column heater coupled to the sample injector. FIGS. 2C and 2D show schematic diagrams of a sample injector 200. Sample injector 200 includes a sample needle 210, a needle port 225, tubing 215 and outlet connector 220. Outlet connector 220 is used to couple the sample injector 200 to pre-column heater 250. FIG. 2A and FIG. 2B show schematic diagrams of a pre-column heater 250. Pre-column heater 250 includes inlet connector 255, which couples to outlet connector 220. Pre-column heater also includes a heating element 260 which heats the fluid passing through tubing 265. An outlet connector 270 is used to connect the pre-column heater tubing 265 to an inlet of a chromatography column (not shown). In an embodiment, the flow path components of the sample injector 200 and/or the pre-column heater 250 are coated with a low-bind surface coating.

Various wetted surfaces of the chromatographic system can be coated with a low-bind surface coating. The term "wetted surfaces" refers to all surfaces within a separation device (e.g., chromatography column, chromatography injection system, chromatography fluid handling system, frit, etc.). The term can also apply to surfaces within labware or other sample preparation devices (e.g., extraction devices) that come into contact with a fluid, especially a fluid containing an analyte of interest. In some embodiments, only the wetted surfaces of the chromatographic column and the components located upstream of the chromatographic column are low-bind surfaces, coated with the alkylsilyl coatings described herein, while wetted surfaces located downstream of the column are not coated. In other embodiments, all wetted surfaces are coated, including those surfaces downstream of the column. And in certain embodiments, wetted surfaces upstream of the column, through the column, and downstream of the column to the entrance of the inlet to the detector are coated. The coating can be applied to the wetted surfaces via vapor deposition. Similarly, the "wetted surfaces" of labware or other fluid processing devices may benefit from alkylsilyl coatings described herein. The "wetted surfaces" of these devices not only include the fluidic flow path, but also elements that reside within the fluidic flow path. For example, frits and/or membranes within a solid phase extraction device come in contact with fluidic samples. As a result, not only the internal walls within a solid phase extraction device, but also any frits/needle ports/membranes are included within the scope of "wetted surfaces." All "wetted surfaces" or at least some portion of the "wetted surfaces" can be improved or tailored for a particular analysis or procedure by including one or more of the coatings described herein.

Further information regarding the coating and the deposition of coatings in accordance with the present technology is available in U.S. Patent Application Publication No. 2019/0086371, which is hereby incorporated by reference.

In some examples, coating the flow path includes uniformly distributing the coating about the flow path, such that the walls defining the flow path are entirely coated. In some embodiments, uniformly distributing the coating can provide a uniform thickness of the coating about the flow path. In general, the coating uniformly covers the wetted surfaces such that there are no "bare" or uncoated spots.

Commercially available vapor deposition coatings can be used in the disclosed systems, devices, and methods, including but not limited to Dursan® and Dursox® (commercially available from SilcoTek Corporation, Bellefonte, PA).

Alkylsily coatings can be used as low-bind surface coatings. Alkylsilyl coatings include bis(trichlorosilyl)ethane or bis(trimethoxysilyl)ethane (also known as C2) coatings. In some embodiments, the alkylsilyl coatings include two or more layers. For example, a first layer including C2 can be vapor deposited followed by a second layer of C10 material (n-decyltrichlorosilane) (known herein as a "C2/C10" coating). US Patent Application Publication No. US2019/0086371 (and in particular, Table 1) provides numerous examples of illustrative embodiments of C2 and C2/C10 coatings and how such coatings are applied to surfaces in the flow path.

The coatings described above can be used to create low-bind surface coatings and can tailor a fluidic flow path of a chromatography system for the separation of a sample. The coatings can be vapor deposited. In general, the deposited coatings can be used to adjust the hydrophobicity of internal surfaces of the fluidic flow path that come into contact with a fluid (i.e. wetted surfaces or surfaces coming into contact with the mobile phase and/or sample/analyte). By coating wetted surfaces of one or more components of a flow path within a chromatography system, a user can tailor the wetted surfaces to provide a desired interaction (e.g., a lack of interaction) between the flow path and fluids therein (including any sample, such as a sample containing tyrosine kinase inhibitors, within the fluid).

Figure 3:
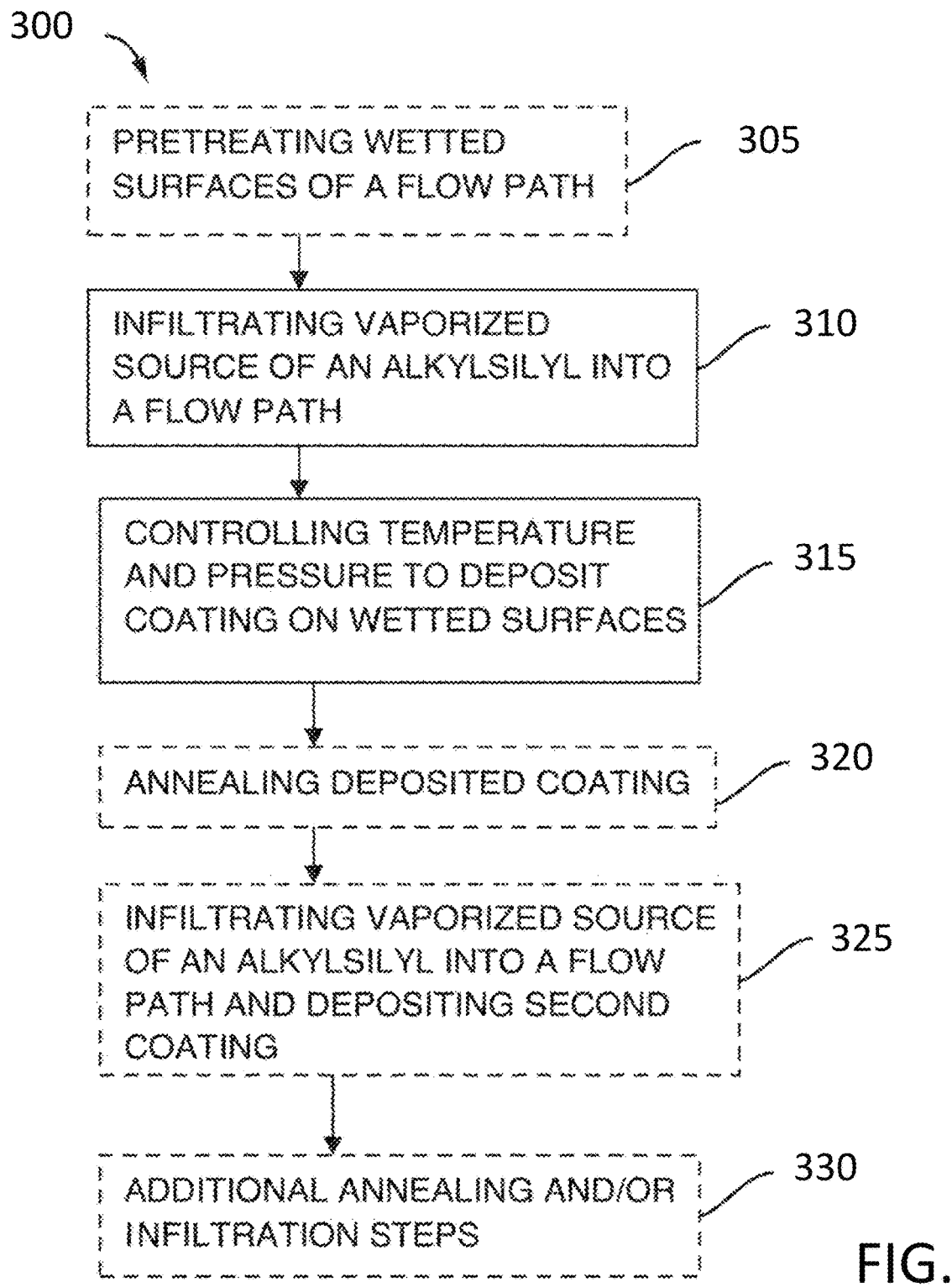
FIG. 3 is a flow chart of a method of coating a fluidic path (such as a fluidic path in a chromatography system) according to an illustrative embodiment of the technology.

FIG. 3 is a flow chart illustrating method 300 for creating a low-binding surface coating by tailoring a fluidic flow path for separation of tyrosine kinase inhibitors. The method has certain steps which are optional as indicated by the dashed outline surrounding a particular step. Method 300 can start with a pretreatment step (305) for cleaning and/or preparing a flow path within a component for tailoring. Pretreatment step 305 can include cleaning the flow path with plasma, such as oxygen plasma. This pretreatment step is optional.

Next, an infiltration step (310) is initiated. A vaporized source of an alkylsilyl compound is infiltrated into the flow path. The vaporized source is free to travel throughout and along the internal surfaces of the flow path. Temperature and/or pressure is controlled during infiltration such that the vaporized source is allowed to permeate throughout the internal flow path and to deposit a coating from the vaporized source on the exposed surface (e.g., wetted surfaces) of the flow path as shown in step 315. Additional steps can be taken to further tailor the flow path. For example, after the coating is deposited, it can be heat treated or annealed (step 320) to create cross linking within the deposited coating and/or to adjust the contact angle or hydrophobicity of the coating. Additionally, or alternatively, a second coating of alkylsilyl compound (having the same or different form) can be deposited by infiltrating a vaporized source into the flow path and depositing a second or additional layers in contact with the first deposited layer as shown in step 325. After the deposition of each coating layer, an annealing step can occur. Numerous infiltration and annealing steps can be provided to tailor the flow path accordingly (step 330).

Figure 4:
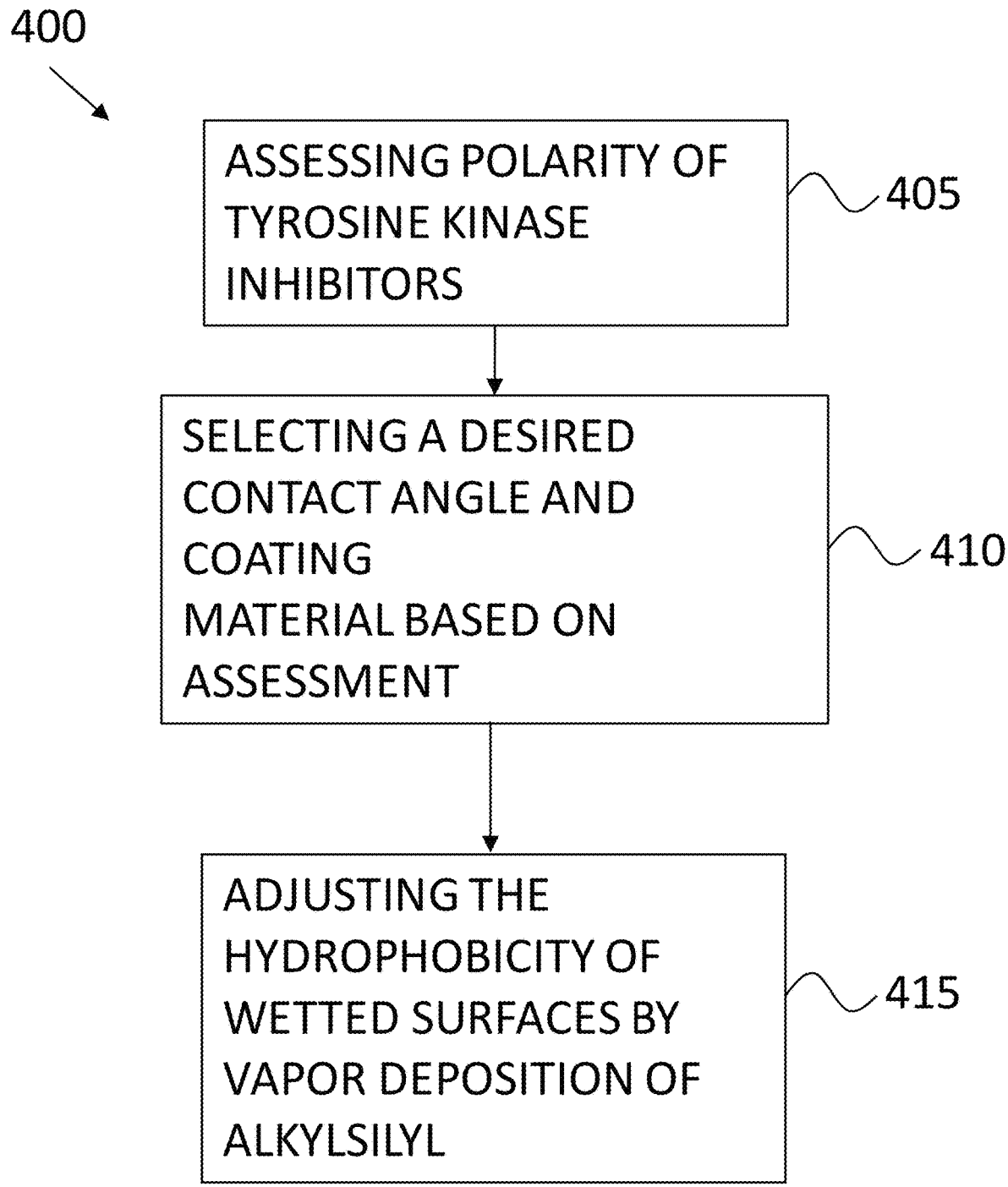
FIG. 4 is a flow chart showing a method of tailoring a fluidic flow path for separation of a sample including tyrosine kinase inhibitors, in accordance with an illustrative embodiment of the technology.
Figure 5B:
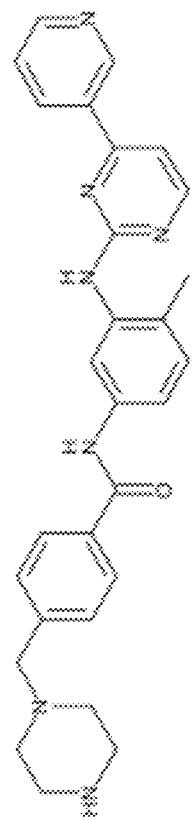
FIG. 5B shows chemical structure of tyrosine kinase inhibitor metabolite norimatinib
Figure 5D:
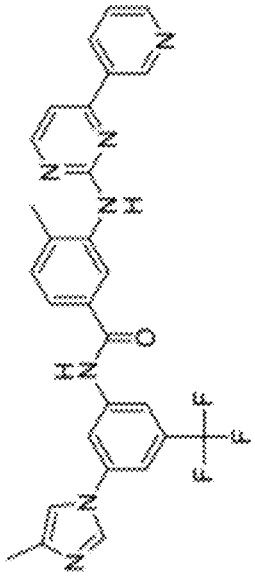
FIG. 5D shows chemical structure of tyrosine kinase inhibitor nilotinib.
Figure 5A:
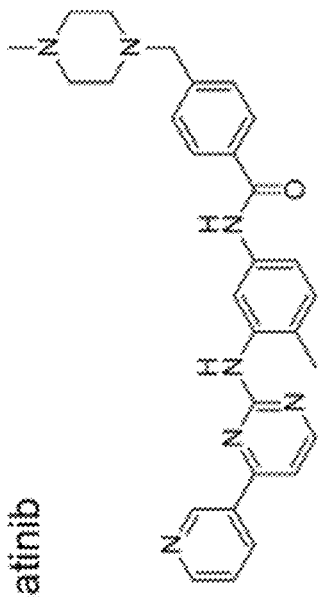
FIG. 5A shows chemical structure of tyrosine kinase inhibitor imatinib.
Figure 5C:
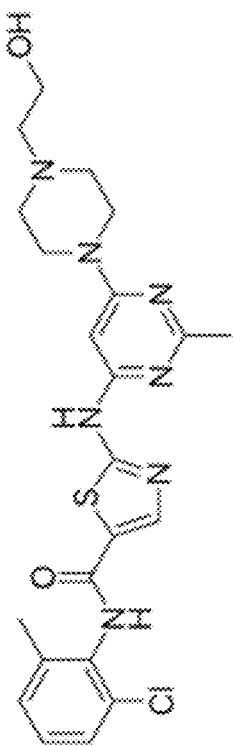
FIG. 5C shows chemical structure of tyrosine kinase inhibitor dasatinib.

FIG. 4 provides a flow chart illustrating a method (400) of creating a low-bind surface coating by tailoring a fluidic flow path for separation of a sample including an analyte, such as TKIs or TKI metabolites. The method can be used to tailor a flow system for use in isolating, separating, and/or analyzing TKIs and TKI metabolites. In step 405, TKIs and/or TKI metabolites are assessed to determine polarity. Understanding the polarity will allow an operator to select (by either look up table or make a determination) a desired coating chemistry and, optionally, contact angle as shown in step 410.

In some embodiments, in addition to assessing the polarity of TKIs and/or TKI metabolites, the polarity of a stationary phase to be used to separate the TKIs and/or TKI metabolites (e.g., stationary phase to be included in at least a portion of the fluidic flow path) is also assessed. A chromatographic media (e.g., stationary phase) can be selected based on metal-sensitive compounds, e.g., TKIs and/or TKI metabolites, in the sample. Understanding the polarity of metal-sensitive compounds and the stationary phase is used in certain embodiments by the operator to select the desired coating chemistry and contact angle in step 410. The components to be tailored can then be positioned within a chemical infiltration system with environmental control (e.g., pressure, atmosphere, temperature, etc.) and precursor materials are infiltrated into the flow path of the component to deposit one or more coatings along the wetted surfaces to adjust the hydrophobicity as shown in step 415. During any one of infiltration, deposition, and condition steps (e.g. annealing), coatings deposited from the infiltration system can be monitored and if necessary precursors and or depositing conditions can be adjusted if required allowing for fine tuning of coating properties.

For analysis of TKIs and/or TKI metabolites, the samples are typically obtained from a subject undergoing cancer therapy by treatment with TKIs. The samples are obtained from the subject by drawing a blood sample from the patient. Either serum or plasma can be extracted from the blood sample for testing. Plasma is separated from the blood sample by centrifugation in the presence of an anticoagulant. Serum is also separated from the blood sample by centrifugation, however, the blood is allowed to clot before the separation. The TKI being administered to the patient, and/or metabolites of the TKI being administered, are present in the plasma or serum extracted from the subject's blood sample. The use of either plasma or serum is preferred for TKI analysis or testing.

EXAMPLES

Prior to any comparisons of coated column/hardware performance versus uncoated column/hardware performance for TKI and TKI metabolite samples, the following protocols were developed and used for sample preparation and analysis.

Sample Preparation

Plasma or serum, obtained from a subject, is used for analysis. 50 µL of plasma or serum is transferred into a 2 mL plastic microtube as the test sample. 250 µL of an internal standard (e.g., deuterated MeOH mixture) is added to the test sample. The microtube is capped and shaken on a flat-bed shaker at 2500 rpm for 30 seconds. The test sample is centrifuged at 16,100 g for 2 minutes. 100 μL of supernatant from the centrifuged test sample is transferred to a 1 mL, 96 well plate. Other samples may be prepared and added to the plate according to this procedure. Once all samples have been added, 300 μL of LC-MS grade water is added to each well containing a sample. The 96 well plate is sealed and centrifuged at 3847 g for 2 minutes. The resulting supernatant was injected into the chromatography system for TKI and/or TKI metabolite analysis For purposes of testing the effect of low bind surfaces on the analysis of TKIs and/or TKI metabolites, test samples were prepared. One set of test samples were prepared by dissolving imatinib, norimatinib, dasatinib, and nilotinib in 25% methanol as exemplary TKIs. Chemical structures of these compounds are depicted in FIGS. 5A-5D. A test sample was also prepared with norimatinib, a metabolite of the TKI imatinib. The following concentrations were used in the test samples: imatinib, 10 ng/mL; norimatinib, 10 ng/mL; dasatinib, 4 ng/mL; and nilotinib 2 ng/mL. Test plasma samples were also prepared by spiking plasma with the stock solution of the sample to give the listed concentration of the sample in plasma: imatinib, 50 ng/mL; norimatinib, 50 ng/mL; dasatinib, 20 ng/mL; and nilotinib 10 ng/mL Each test sample was analyzed on an ACQUITY UPLC I-Class chromatography system (Waters Corporation, Milford, MA) using a Xevo TQD mass spectrometer (Waters Corporation, Milford) as the detector. The same system was used for both non-treated surfaces and low binding surfaces. For tests performed with low binding surfaces, tests were performed by replacing the standard sample needle with a C2 or C2/C10 coated sample needle. The pre-column heater was replaced by a pre-column heater having C2 or C2/C10 tubing.

As shown in Tables 1 and 2, the same UPLC Conditions and the same gradient mobile phase was used for both non-treated surfaces and low binding surfaces. Mass spectroscopy conditions were also the same for both non-treated surfaces and low binding surfaces and are set forth in Tables 3 and 4.

TABLE 1

UPLC Conditions

| Parameter | Description |
|---|---|
| System | I-Class/FTN IVD, 30 μL needle |
| Column | ACQUITY UPLC ® BEH Phenyl 2.1 × 50 mm (P/N 186002884) |
| Injection Volume | 5 μL |
| Temperature | 50° C. |
| Mobile Phase A | Water + 2 nM Ammonium acetate + 0.1% formic acid |
| Mobile Phase B | Methanol + 2 nM Ammonium acetate + 0.1% formic acid |
| Flow rate | 0.4 mL/min |
| Gradient | See Table 2 - A saw-toothed gradient was used to reduce carryover |

TABLE 2

Gradient Timetable

| Time (mins) | A (%) | B (%) | Curve |
|---|---|---|---|
| 0.00 | 60 | 40 | 1 |
| 2.00 | 55 | 45 | 6 |
| 2.01 | 2 | 98 | 11 |
| 2.91 | 98 | 2 | 11 |
| 3.11 | 2 | 98 | 11 |
| 3.31 | 98 | 2 | 11 |
| 3.51 | 2 | 98 | 11 |
| 3.71 | 98 | 2 | 11 |
| 3.91 | 60 | 40 | 11 |

TABLE 3

MS Conditions - Xevo TQD

| Parameter | Description |
|---|---|
| Ion Mode | ESI +ve |
| Capillary | 0.8 kV |
| Source Temperature | 150° C. |
| Desolvation Temperature | 500° C. |
| Desolvation Gas Flow | 800 L/Hr |
| MS1/MS2 Resolution | Unit/Unit |

TABLE 4

MRM Parameters

| Compound | Channel | Dwell (s) | Cone (V) | Collision (eV) |
|---|---|---|---|---|
| Norimatinib (Quan) | 480.2 > 394.2 | 0.04 | 40 | 26 |
| Dasatinib (Quan) | 488.2 > 401.2 | 0.04 | 50 | 28 |
| Imatinib (Quan) | 494.2 > 394.2 | 0.04 | 40 | 26 |
| Nilotinib (Quan) | 530.2 > 289.1 | 0.02 | 52 | 30 |

Comparative Testing of the Effect of Low-Bind Surface Coatings on TKIs and TKI Metabolites Four different test configurations were initially used to test the effect of C2/C10 low-bind surface coatings on the analysis of TKIs and TKI metabolites. The initial test configurations are set forth in Table 5 below.

TABLE 5

Test Configurations

| Configuration | Pre-column heater | Needle |
|---|---|---|
| 1 | Original | Original |
| 2 | Low-bind | Low-bind |
| 3 | Low-bind | Original |
| 4 | Original | Low-bind |

Figure 6B:
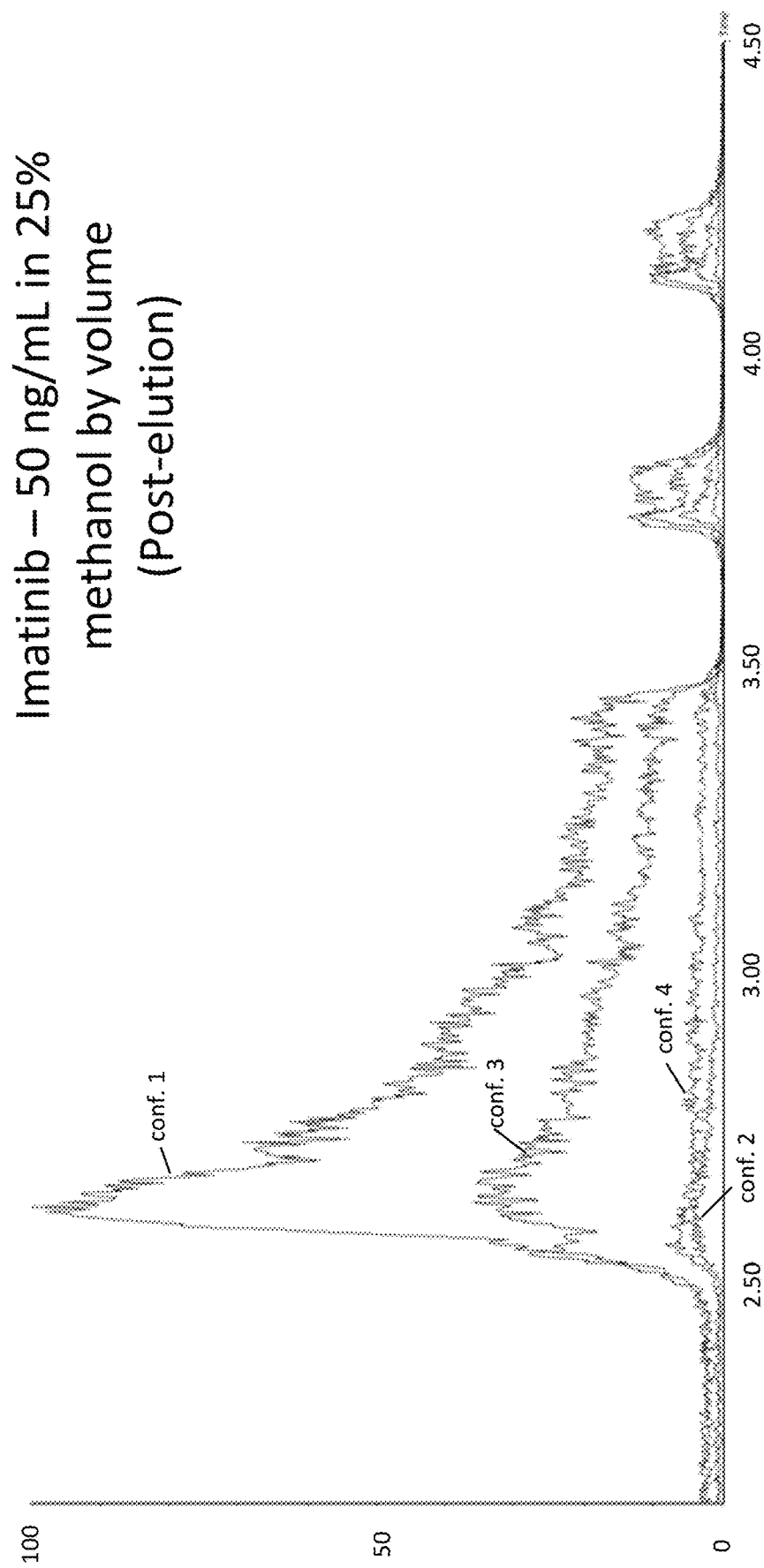
FIG. 6B shows an overlay of chromatograms in the carry-over region obtained from HPLC analysis of a sample of imatinib in methanol (25% by volume) using four different chromatography system configurations having different combinations of original (uncoated) and coated components (sample needle and/or pre-column heater).

Initial test results showed that use of C2/C10 low-bind surface coatings in either the sample needle, the pre-column heater, or both resulted in improved peak height, improved peak shape, and reduced carryover, compared to test performed using original equipment. Exemplary results of tests with these configurations on imatinib are shown in FIG. 6A and FIG. 6B. FIG. 6A shows an overlay of the chromatograms for each of the runs. FIG. 6B shows a close up of the chromatogram at the 2 min. to 4.5 min range. In FIG. 6A, the smallest peak (1.3), largest carryover (2.6) is configuration 1—original pre-column heater (PCH)/original needle. The 2nd smallest peak, 2nd largest carryover is configuration 3—low bind PCH/original needle. The 2nd largest peak, 2nd smallest carryover is configuration 4—original PCH/low bind needle. The largest peak, smallest carryover is configuration 2—low bind PCH/low bind needle. The use of low-bind surface coating on the components improved peak height and reduced tailing, compared to original components. The use of both a pre-column heater having low-bind surface coating and a sample needle having a low-bind surface coating produced the greatest improvements in peak height and tailing. In FIG. 6B, the largest carryover is configuration 1—original PCH/original needle; 2nd largest carryover is configuration 3—low bind PCH/original needle; 2nd smallest carryover is configuration 4—original PCH/low bind needle; and smallest carryover is configuration 2, low bind PCH/low bind needle. The use of both a pre-column heater having low-bind surface coating and a sample needle having a low-bind surface coating produced the least amount of carryover. Replacement of the sample needle with a sample needle having a low-bind surface coating produces a greater effect than replacement of the pre-column heater components with components having low-bind surface coatings.

Using Configurations 1 and 2, comparative tests were run using test samples of imatinib, 50 ng/mL; norimatinib, 50 ng/mL; dasatinib, 20 ng/mL; and nilotinib 10 ng/mL spiked in plasma as set forth previously.

Figure 7A:
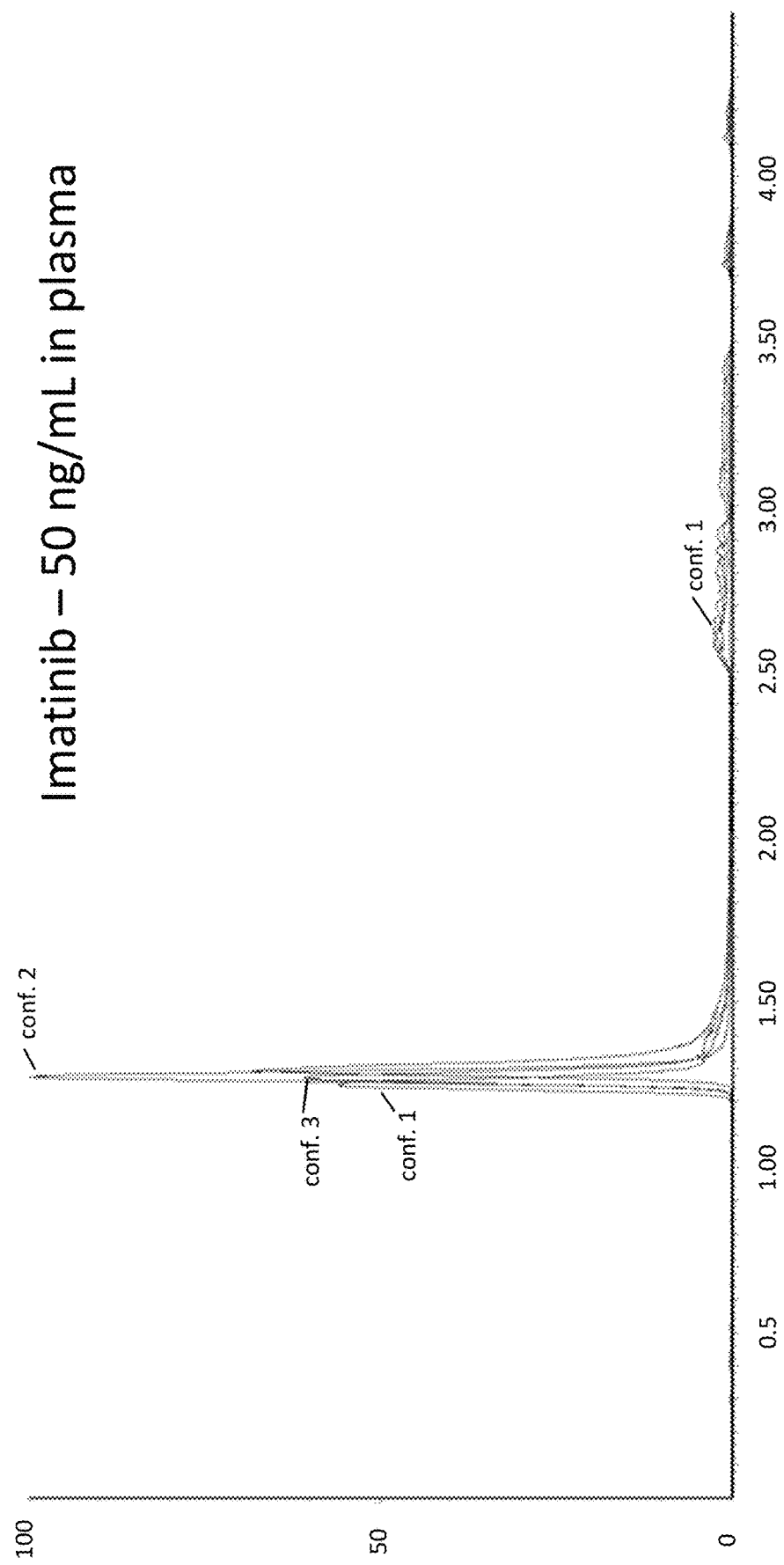
FIG. 7A shows an overlay of chromatograms obtained from HPLC analysis of a sample of imatinib in plasma using chromatography system configurations having either original (uncoated) components or coated components (sample needle and pre-column heater).
Figure 7B:
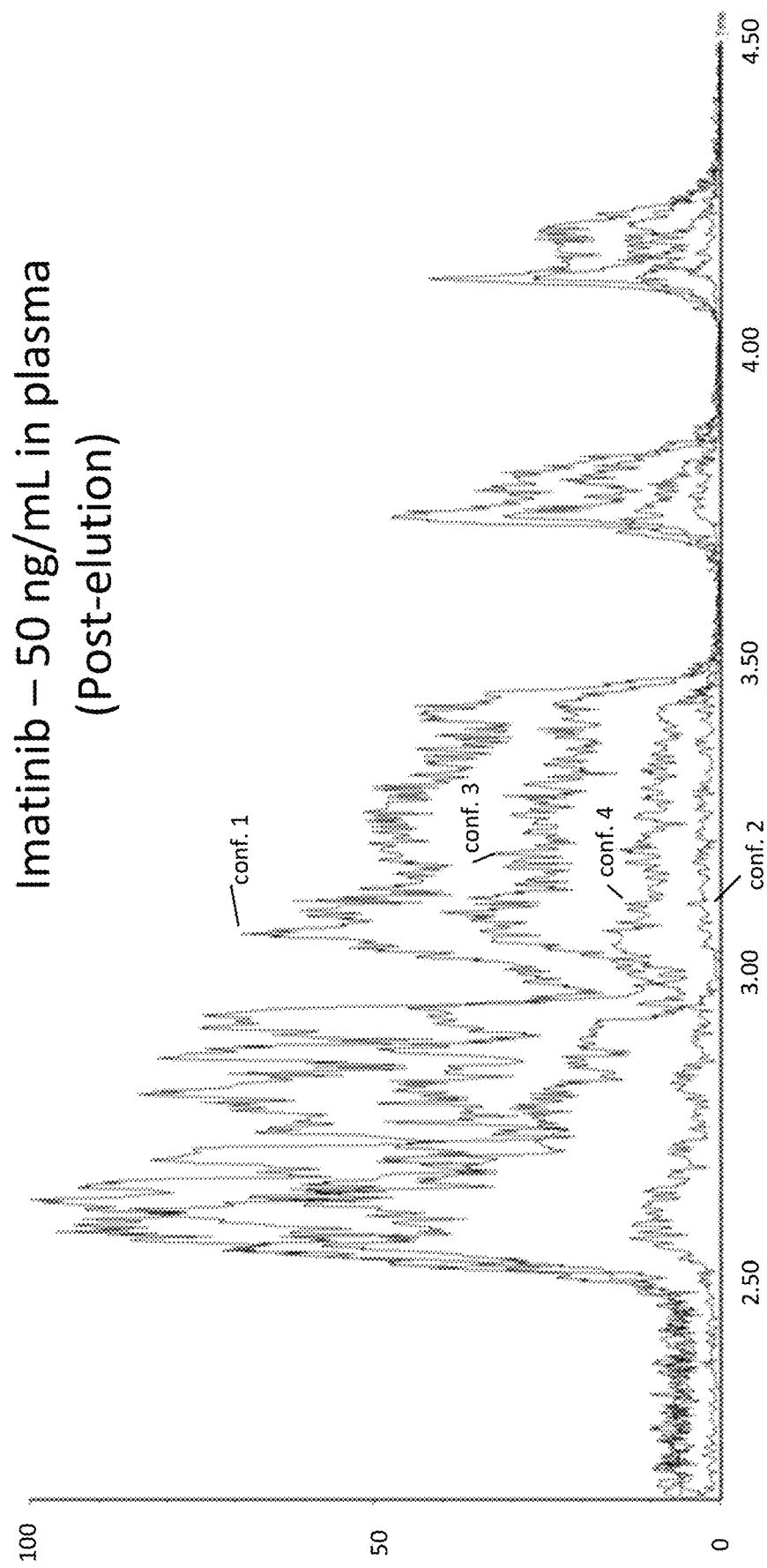
FIG. 7B shows an overlay of chromatograms in the carry-over region obtained from HPLC analysis of a sample of imatinib in plasma using chromatography system configurations having either original (uncoated) components or coated components (sample needle and pre-column heater).

FIGS. 7A and 7B show comparative traces of imatinib in plasma using original parts (non-coated) compared to C2/C10 coated parts. In FIG. 7A the smallest peak, largest carryover is configuration 1—original PCH/original needle; $2^{nd}$ smallest peak, $2^{nd}$ largest carryover is configuration 3—low bind PCH/original needle; $2^{nd}$ largest peak, $2^{nd}$ smallest carryover is configuration 4—original PCH/low bind needle; largest peak, smallest carryover is configuration 2, low bind PCH/low bind needle. These results show a 3-fold increase in peak height when using a C2/C10 coated pre-column heater and needle, compared to original components. FIG. 7B shows an enlarged view of the region from 2.2 min. to 4.5 minute, which represents the carryover material. In FIG. 7B, the largest carryover is configuration 1—original PCH/original needle; $2^{nd}$ largest carryover is configuration 3—low bind PCH/original needle; $2^{nd}$ smallest carryover is configuration 4—original PCH/low bind needle; smallest carryover is configuration 2, low bind PCH/low bind needle. As shown, there is an 8-fold reduction in carryover maximum signal height using a C2/C10 coated pre-column heater and needle, compared to original components.

Figure 8A:
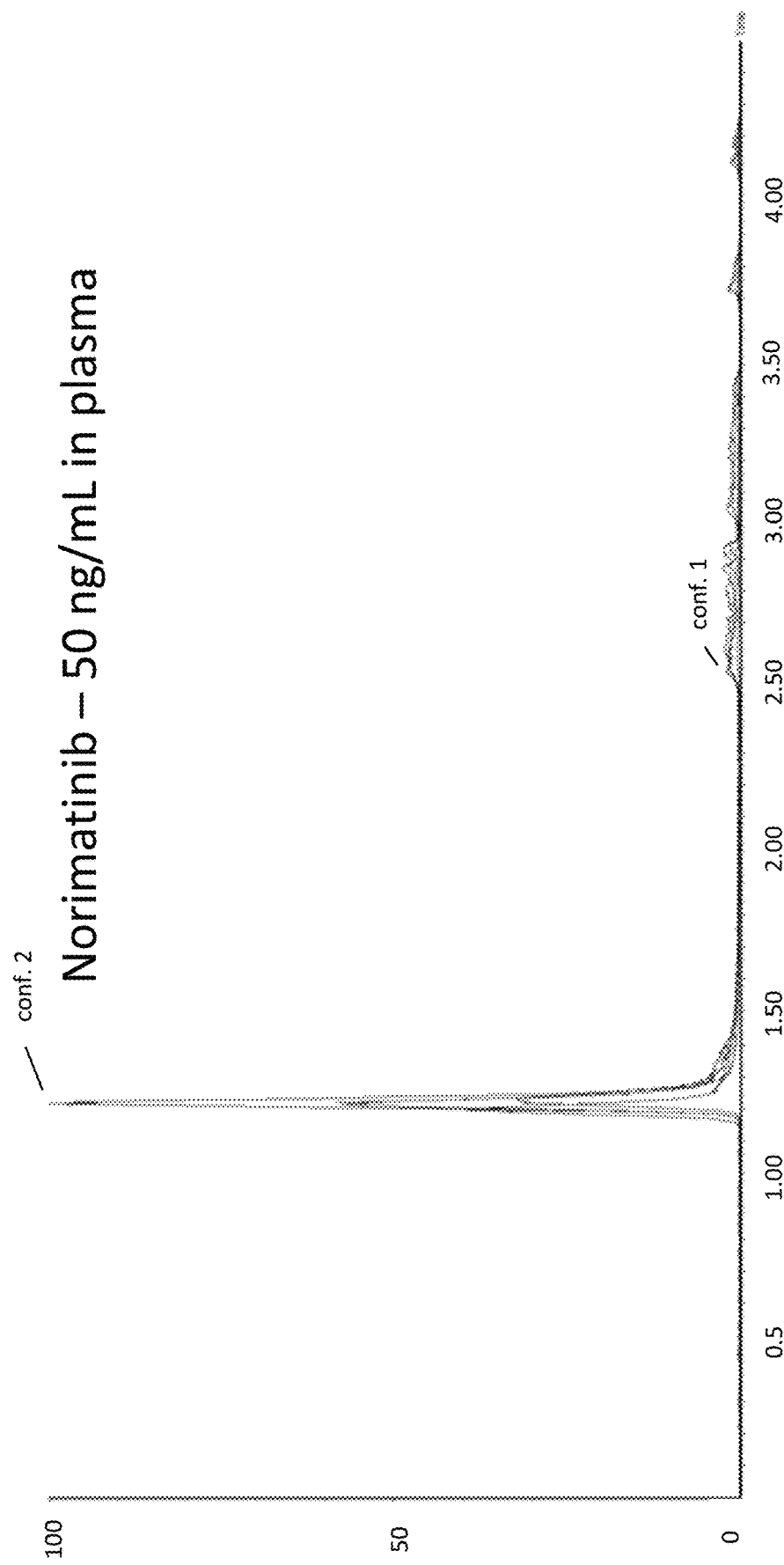
FIG. 8A shows an overlay of chromatograms obtained from HPLC analysis of a sample of norimatinib in plasma using chromatography system configurations having either original (uncoated) components or coated components (sample needle and pre-column heater).
Figure 8B:
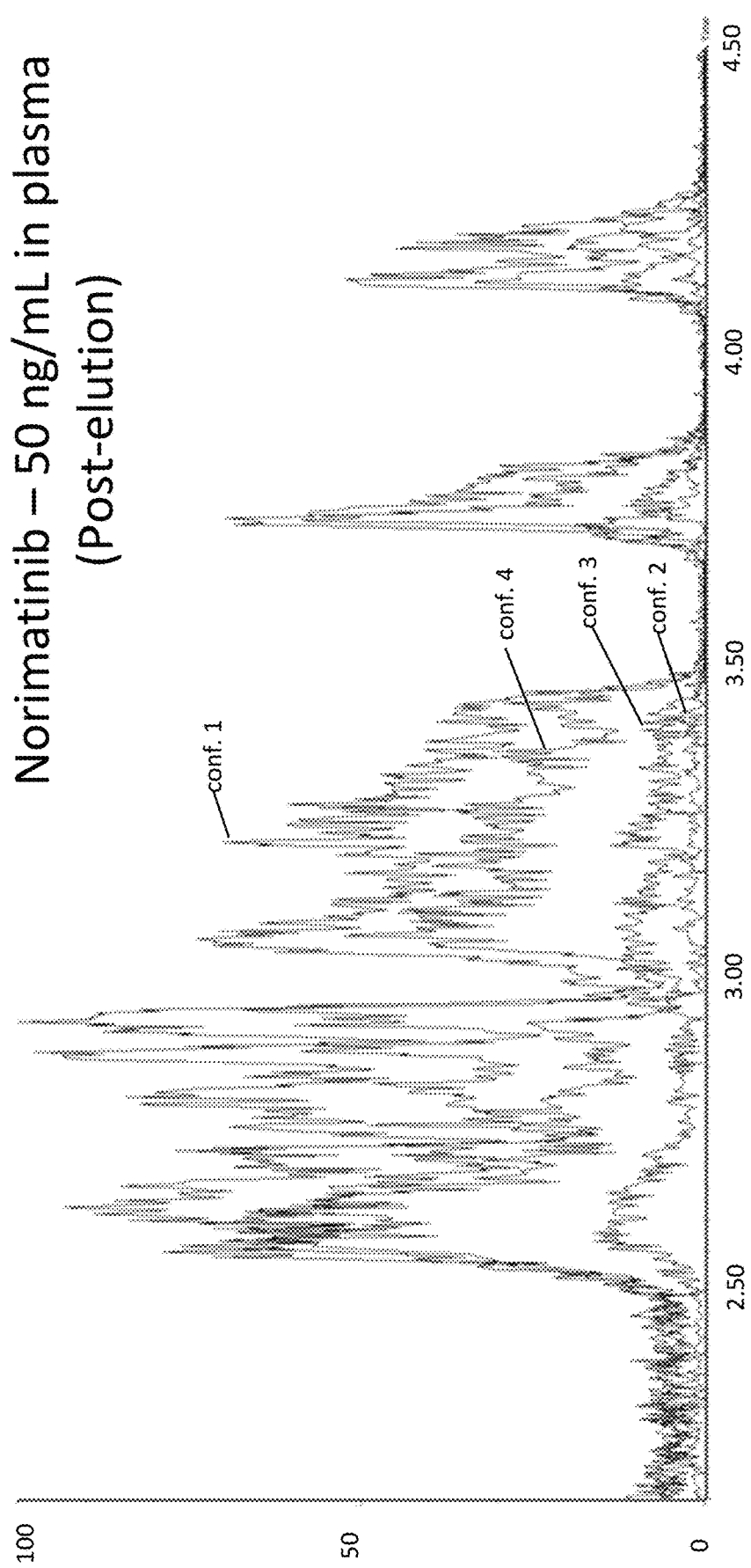
FIG. 8B shows an overlay of chromatograms in the carry-over region obtained from HPLC analysis of a sample of norimatinib in plasma using chromatography system configurations having either original (uncoated) components or coated components (sample needle and pre-column heater).

FIG. 8A shows comparative traces of norimatinib in plasma using original parts (non-coated) compared to C2/C10 coated parts. Norimatinib is the N-desmethyl metabolite of imatinib. In FIG. 8A, the smallest peak is from configuration 4—original PCH/low bind needle; $2^{nd}$ smallest peak is configuration 1—original PCH/original needle; $2^{nd}$ largest peak is configuration 3—original PCH/low bind needle; largest peak, smallest carryover is configuration 2, low bind PCH/low bind needle. The results show a 4-fold increase in peak height when using a C2/C10 coated pre-column heater and needle, compared to original components. FIG. 8B shows an enlarged view of the region from 2.2 min. to 4.5 minute, which represents the carryover material. In FIG. 8B, the largest carryover is configuration 1—original PCH/original needle; $2^{nd}$ largest carryover is configuration 4—original PCH/low bind needle; $2^{nd}$ smallest carryover is configuration 3—low bind PCH/original needle; and smallest carryover is configuration 2, low bind PCH/low bind needle. As shown, there is a 3-fold reduction in carryover maximum signal height using a C2/C10 coated pre-column heater and needle, compared to original components.

Figure 9A:
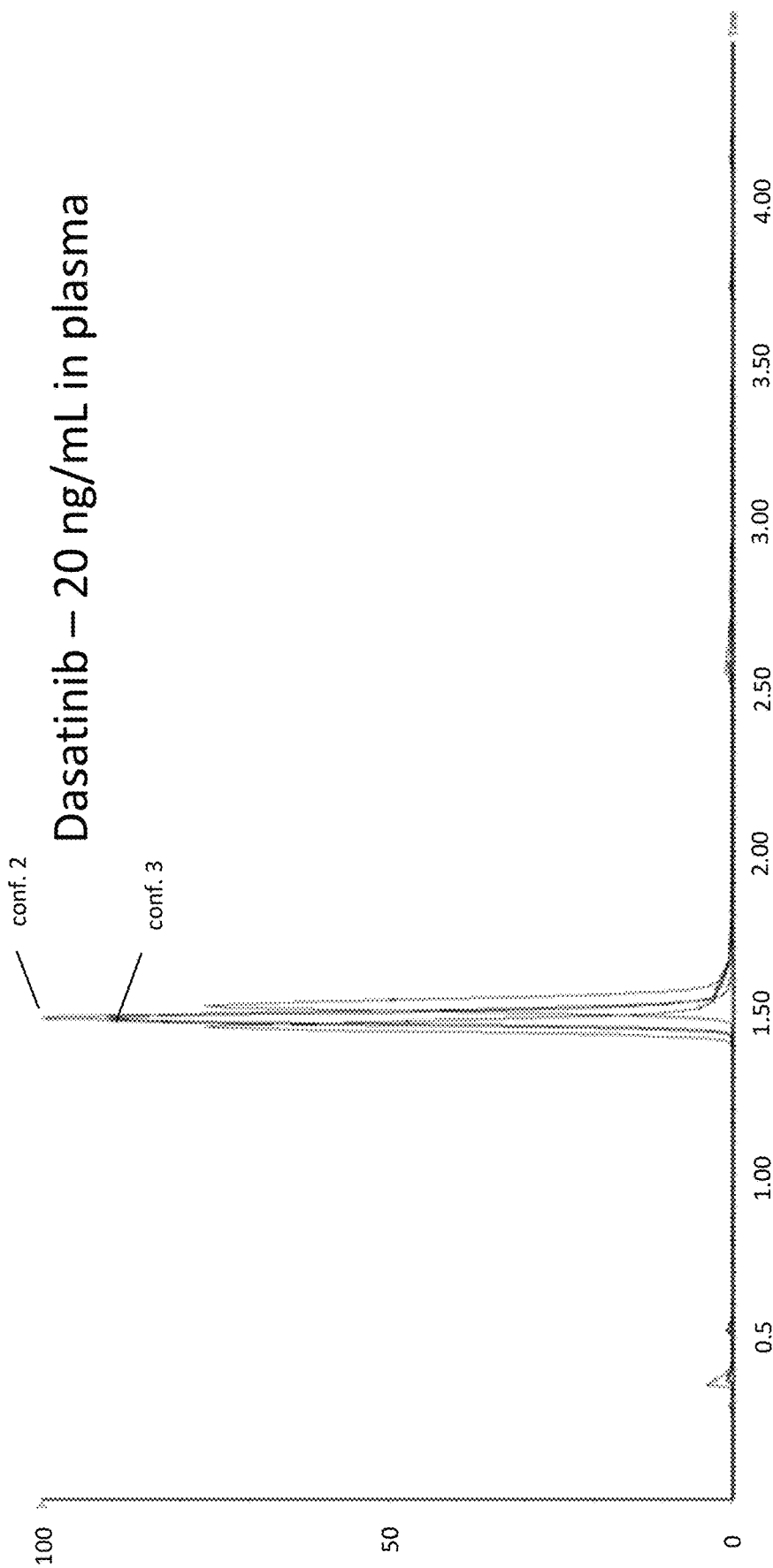
FIG. 9A shows an overlay of chromatograms obtained from HPLC analysis of a sample of dasatinib in plasma using chromatography system configurations having either original (uncoated) components or coated components (sample needle and pre-column heater).
Figure 9B:
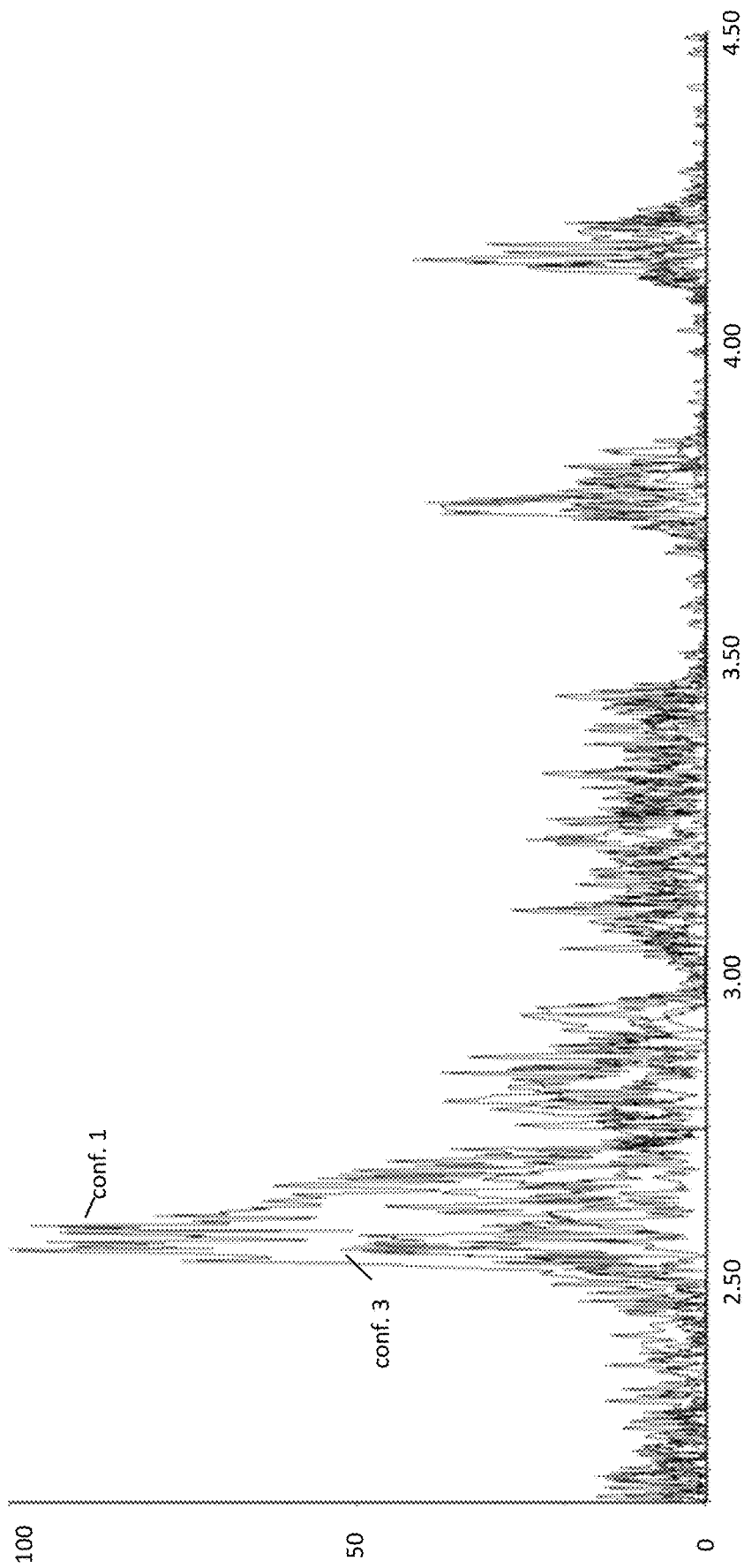
FIG. 9B shows an overlay of chromatograms in the carry-over region obtained from HPLC analysis of a sample of dasatinib in plasma using chromatography system configurations having either original (uncoated) components or coated components (sample needle and pre-column heater).

FIG. 9A shows comparative traces of dasatinib in plasma using original parts (non-coated) compared to C2/C10 coated parts. In FIG. 9A, the smallest peak/earlier eluting is configuration 1—original PCH/original needle; the smallest peak, later eluting is configuration 4—original PCH/low bind needle; $2^{nd}$ largest peak is configuration 3—original PCH/low bind needle; largest peak, smallest carryover is configuration 2—low bind PCH/low bind needle. The results show a 1.5-fold increase in peak height when using a C2/C10 coated pre-column heater and needle, compared to original components. FIG. 9B shows an enlarged view of the region from 2.2 min. to 4.5 minute, which represents the carryover material. In FIG. 9B, the largest carryover is configuration 1—original PCH/original needle; $2^{nd}$ largest carryover is configuration 3—low bind PCH/original needle; $2^{nd}$ smallest carryover is configuration 4—original PCH/low bind needle; smallest carryover is configuration 2, low bind PCH/low bind needle. As shown, there is a 4-fold reduction in carryover maximum signal height using a C2/C10 coated pre-column heater and needle, compared to original components.

Figure 10A:
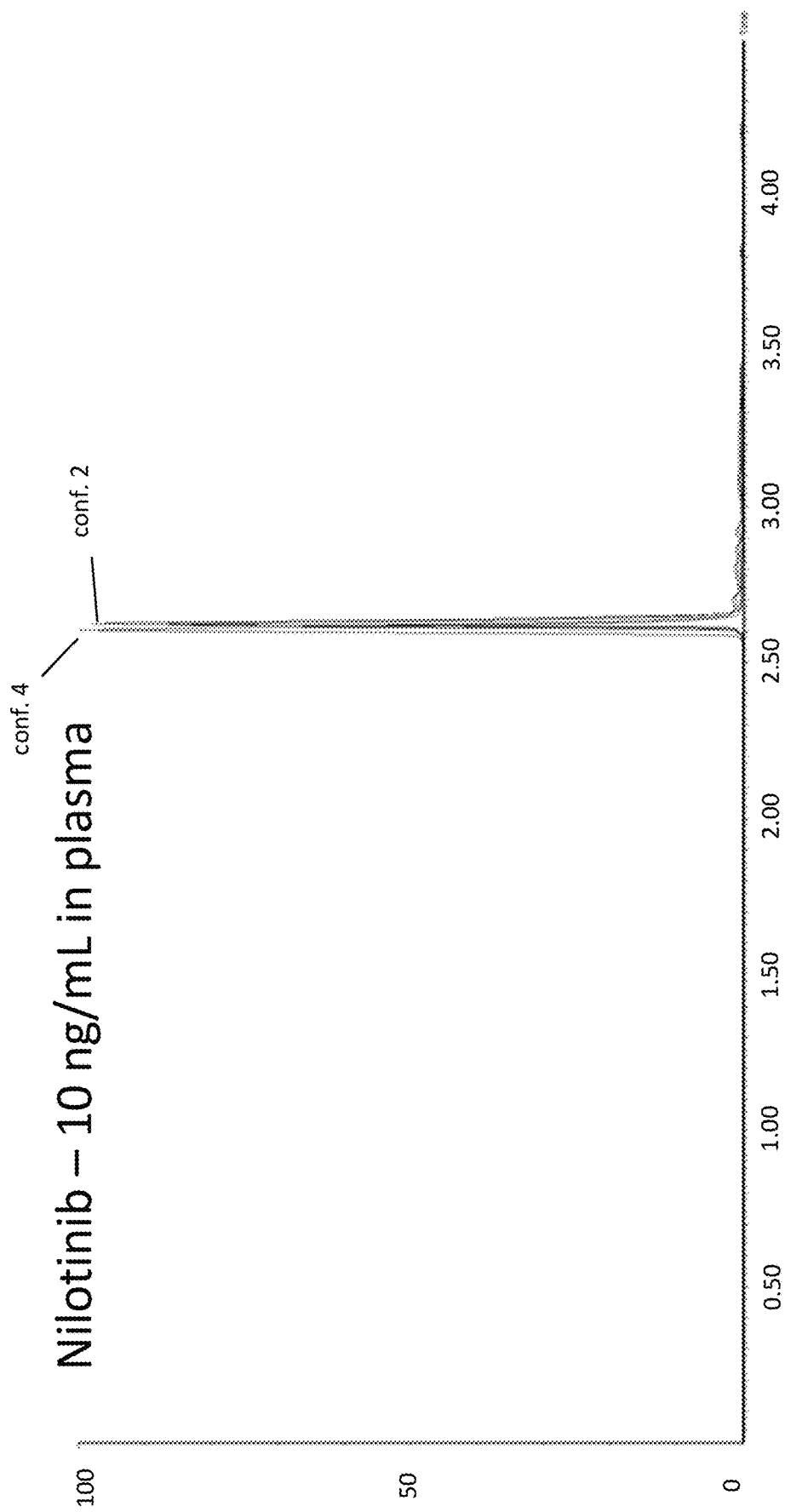
FIG. 10A shows an overlay of chromatograms obtained from HPLC analysis of a sample of nilotinib in plasma using chromatography system configurations having either original (uncoated) components or coated components (sample needle and pre-column heater).
Figure 10B:
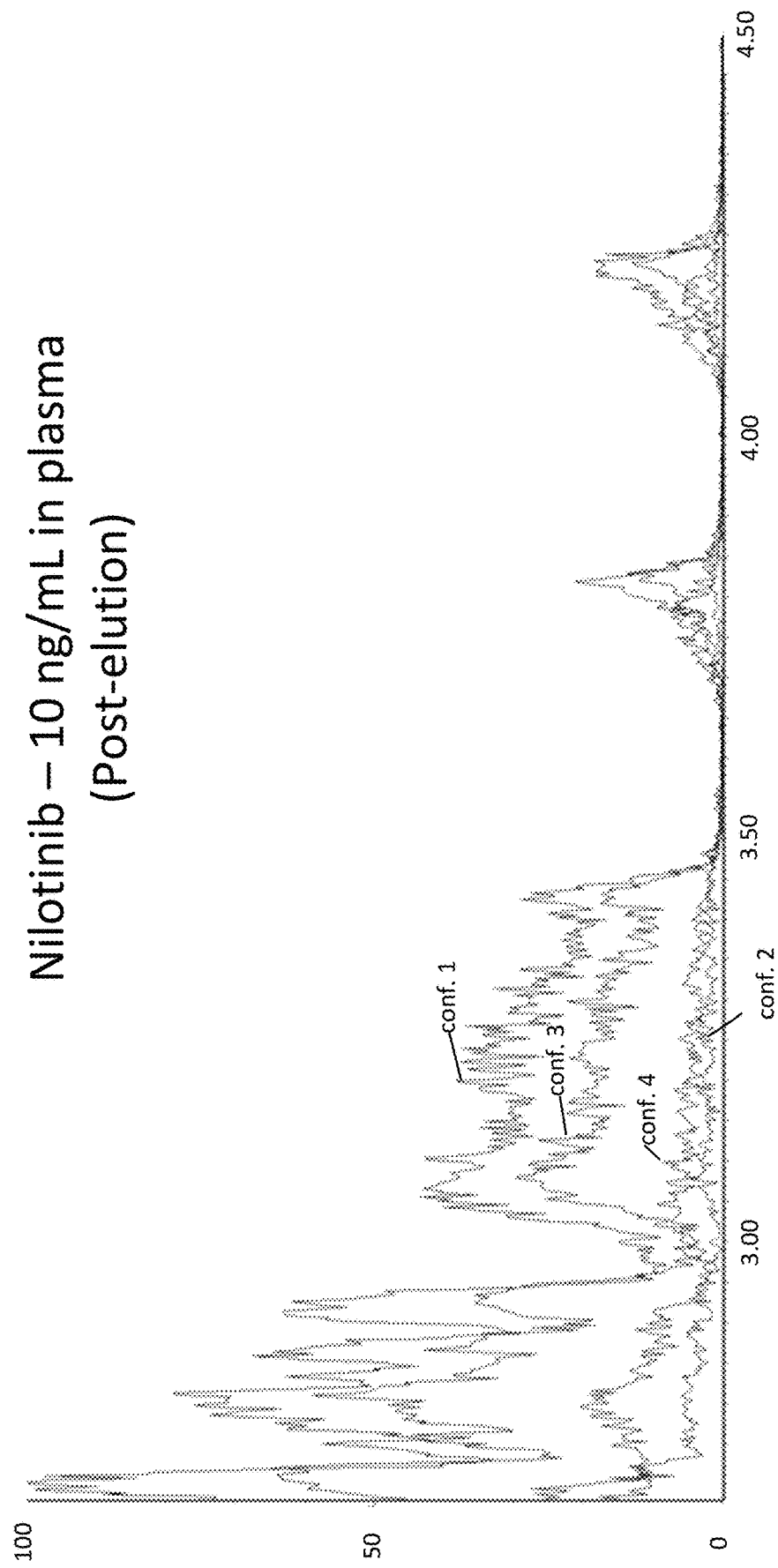
FIG. 10B shows an overlay of chromatograms in the carry-over region obtained from HPLC analysis of a sample of nilotinib in plasma using chromatography system configurations having either original (uncoated) components or coated components (sample needle and pre-column heater).

FIG. 10A shows comparative traces of nilotinib in plasma using original parts (non-coated) compared to C2/C10 coated parts. In FIG. 10A, the largest peak, earlier eluter is configuration 4—original PCH, low bind needle; $2^{nd}$ largest peak, later eluter is configuration 2, low bind PCH/low bind needle; $3^{rd}$ largest peak is configuration 3—low bind PCH/original needle; smallest peak is configuration 1—original PCH/original needle. The results show a 1.7-fold increase in peak height when using a C2/C10 coated pre-column heater and needle, compared to original components. FIG. 10B shows an enlarged view of the region from 2.7 min. to 4.5 minute, which represents the carryover material. FIG. 10B, the largest carryover is configuration 1—original PCH/original needle; $2^{nd}$ largest carryover is configuration 3—low bind PCH/original needle; $2^{nd}$ smallest carryover is configuration 4—original PCH/low bind needle; smallest carryover is configuration 2, low bind PCH/low bind needle. As shown, there is a 5-fold reduction in carryover maximum signal height using a C2/C10 coated pre-column heater and needle, compared to original components.

Figure 11:
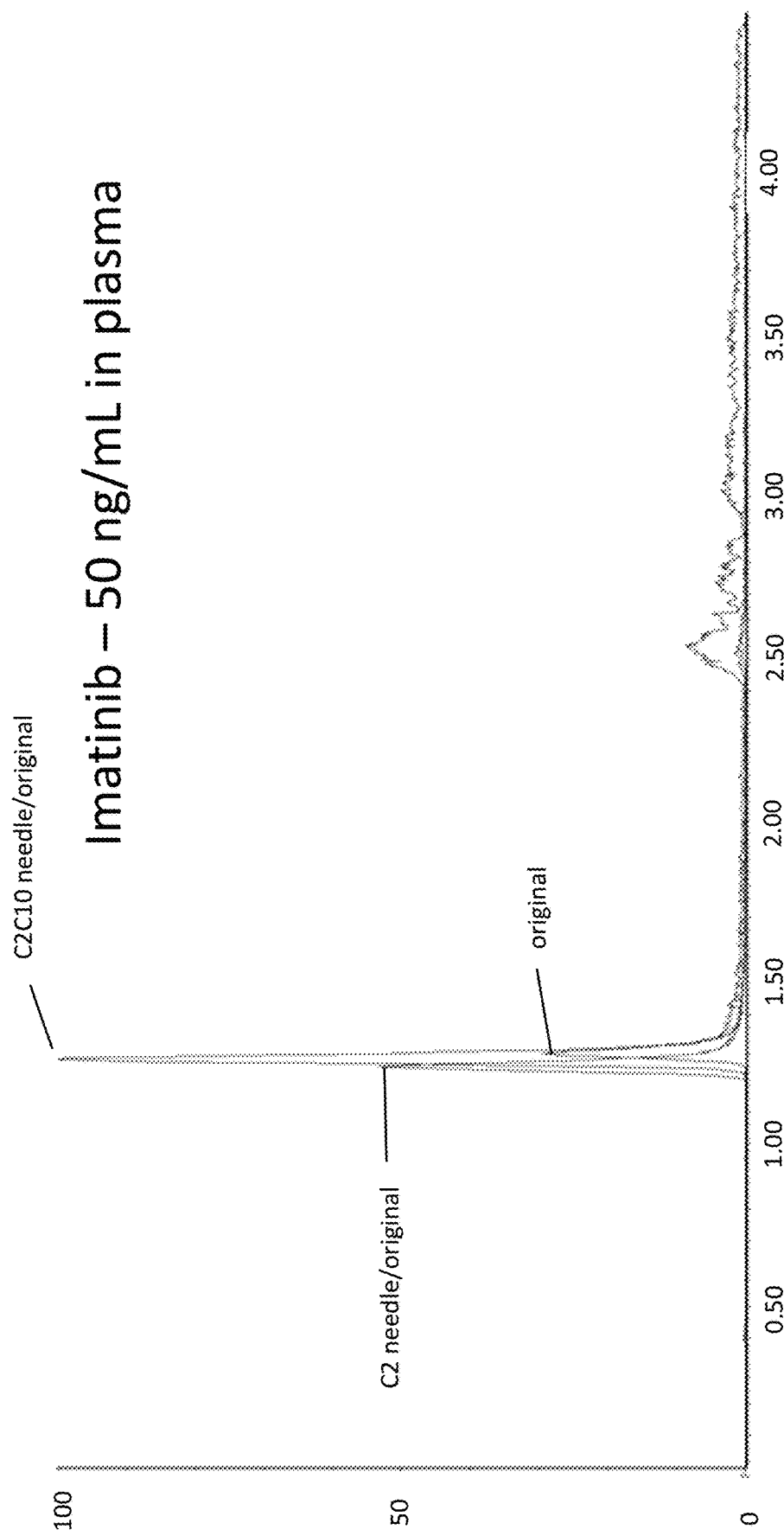
FIG. 11 shows an overlay of chromatograms obtained from HPLC analysis of a sample of imatinib in plasma using chromatography system configurations having either original (uncoated) components or a C2 coated sample needle, or a C2/C10 coated sample needle.

In another experiment, the effect of C2 coated components (single coating) was compared to C2/C10 coated components (two coating layers). FIG. 11 shows a comparison of original components, C2 components, and C2/C10 components during testing for imatinib. In FIG. 11, the smallest peak is original needle/original other components; $2^{nd}$ largest peak is C2 needle/original other components; largest peak is C2/C10 needle/original other components. The peak height is highest and carryover is lowest when a C2/C10 coating is used on the sample needle, compared to the original (non-coated) components. Use of a C2 coating on the sample needle further improves both peak height and reduces carryover, but not as much as the C2/C10 coated surfaces.

Figure 12:
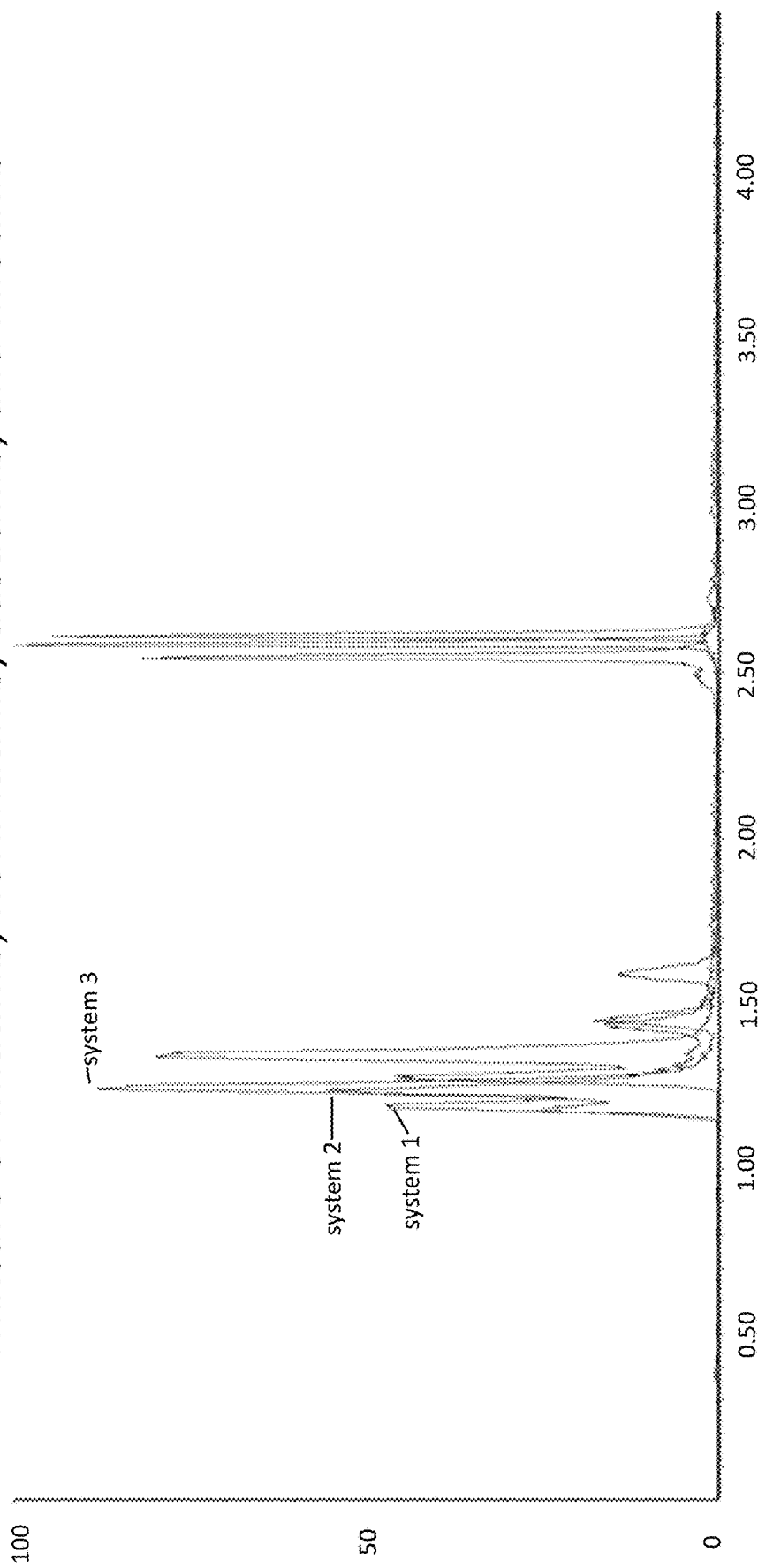
FIG. 12 shows an overlay of chromatograms obtained from HPLC analysis of a sample of a mixture of imatinib, norimatinib, dasatinib, and nilotinib in plasma using chromatography system configurations having System 1: modified to have a C2 needle port, original (uncoated) needle and original (uncoated) pre-column heater; System 2: modified to have a C2 needle port, C2C10 needle, with original (uncoated) pre-column heater; and System 3: modified to have a C2 needle port, C2/C10 needle and a C2/C10 pre-column heater.

In another experiment, the effect of a C2 coated needle port was investigated. In this experiment, a mixture containing imatinib, 50 ng/mL; norimatinib, 50 ng/mL; dasatinib, 20 ng/mL; and nilotinib 10 ng/mL was used for testing. Three different chromatography system setups were used: System 1: modified to have a C2 needle port, original (uncoated) needle and original (uncoated) pre-column heater; System 2: modified to have a C2 needle port, C2C10 needle, with original (uncoated) pre-column heater; and System 3: modified to have a C2 needle port, C2/C10 needle and a C2/C10 pre-column heater. In all three systems, an uncoated chromatography column was used. In FIG. 12, System 3 displays the largest peaks for the TKIS, System 2 the second largest peaks for the TKIs, and System 1 has the smallest peaks for the TKIs. The use of a C2 needle port improved the peak height and shape for each of the TKIs in the mixture. Replacing the original needle with a C2C10 needle significantly improved peak height, even when the pre-column heater uses the original components. The best results were achieved by use of all three coated components (needle port, needle and pre-column heater.

To summarize the results, use of low-bind surface coatings on components of the chromatography system provides a means to instantly improve peak height when analyzing TKIs and TKI inhibitors, in part, by reducing tailing. The use of low bind surface coatings also was shown to reduce carryover when analyzing TKIs and TKI metabolites. It was found that both single low-bind coated components (e.g., C2 coated components) and two-layer low-bind coated components (e.g., C2/C10) improve peak height and reduce carryover when analyzing TKIs and TKI metabolites. C2/C10 coated components provided better results than C2 coated components on peak height and carryover reduction. Further tests show that changing the needle to a C2/C10 or C2 low-bind surface coated component has the most effect on peak height and carryover during analysis of TKIs. Changing the needle port form an uncoated to a C2 low-bind surface coated needle port also improved the peak height and reduction of carryover.

The above aspects and features of the present technology provide numerous advantages over the prior art. For example, the present disclosure shows the benefits of reducing secondary interactions through the use of coated components in the chromatography system. The use of low-bind surface coated components positively impacts chromatographic performance in terms of band broadening, peak tailing, and/or recovery which can then help increase resolution, peak capacity, and/or quantitative accuracy of liquid chromatography-based assays, particularly for liquid chromatography-based TKI assays.

What is claimed is:

1. A method of separating and analyzing tyrosine kinase inhibitors, the method comprising:
    injecting a sample comprising one or more tyrosine kinase inhibitors into a chromatographic system, wherein the sample is prepared from plasma or serum obtained from a subject, and wherein the chromatographic system comprises a metallic flow path, wherein at least a portion of the metallic flow path is coated with a low-bind surface coating;
    flowing the sample through the chromatographic system;
    separating the one or more tyrosine kinase inhibitors from other components in the plasma or serum; and
    passing the separated tyrosine kinase inhibitors to a detector.

2. The method of claim 1, wherein the method further comprises analyzing the separated tyrosine kinase inhibitors to determine an identity and/or amount of tyrosine kinase inhibitors present in the plasma or serum.

3. The method of claim 1, wherein the sample comprises two or more tyrosine kinase inhibitors, and wherein the method further comprises separating the two or more tyrosine kinase inhibitors from each other and determining an identity and/or amount of each separated tyrosine kinase inhibitor.

4. The method according to claim 1, wherein the one or more tyrosine kinase inhibitors comprise at least one of imatinib, norimatinib (N-desmethyl imatinib), dasatinib, and nilotinib.

5. The method according to claim 1, wherein the metallic flow path of the chromatographic system comprises interior wetted surfaces of a sample injector, a pre-column heater coupled to the sample injector and a chromatography column coupled to the pre-column heater, wherein injecting the sample comprises drawing the sample into the chromatographic system through a sample needle of the sample injector and passing the sample through the pre-column heater before the sample enters the chromatography column.

6. The method according to claim 5, wherein the portion of the metallic flow path coated with the low-bind surface coating comprises the interior wetted surfaces of the sample needle.

7. The method according to claim 5, wherein the portion of the metallic flow path coated with the low-bind surface coating comprises the interior wetted surfaces of a needle port of the sample injector.

8. The method according to claim 5, wherein the portion of the metallic flow path coated with the low-bind surface coating comprises the interior wetted surfaces of the pre-column heater.

9. The method according to claim 5, wherein the portion of the metallic flow path coated with the low-bind surface coating comprises the interior wetted surfaces of: a needle port, the sample needle, and the pre-column heater.

10. The method according to claim 1, wherein the low-bind surface coating comprises an alky-silyl coating.

11. The method according to claim 10, wherein the alkylsilyl coating comprises bis(trimethoxysilyl)ethane or bis(tirchlorosilyl)ethane.

12. The method according to claim 10, wherein the alky-silyl coating comprises a first alkylsilyl coating layer in contact with the portion of the metallic flow path and a second alkylsilyl coating layer formed on the first alkylsilyl coating layer.

13. The method according to claim 12, wherein the first coating layer comprises bis(trimethoxysilyl)ethane or bis(tirchlorosilyl)ethane, and wherein the second coating layer comprises n-decyltrichlorosilane.

14. The method of claim 1, wherein the detector is a mass spectrometer.

* * * * *